United States Patent
Schneider et al.

(10) Patent No.: US 12,017,403 B2
(45) Date of Patent: Jun. 25, 2024

(54) SURFACE PROTRUSION FORMATIONS AND METHODS OF MANUFACTURING

(71) Applicant: The Procter & Gamble Company, Cincinnati, OH (US)

(72) Inventors: Uwe Schneider, Cincinnati, OH (US); Michael Devin Long, Harrison Township, OH (US); Justin B. Owens, Ft. Thomas, KY (US); Jeromy Thomas Raycheck, South Lebanon, OH (US); Urmish Popatlal Dalal, Milford, OH (US); Jason Edward Naylor, Loveland, OH (US); Jeffry Rosiak, Loveland, OH (US)

(73) Assignee: The Procter & Gamble Company, Cincinnati, OH (US)

(*) Notice: Subject to any disclaimer, the term of this patent is extended or adjusted under 35 U.S.C. 154(b) by 293 days.

(21) Appl. No.: 17/493,114

(22) Filed: Oct. 4, 2021

(65) Prior Publication Data
US 2022/0106714 A1 Apr. 7, 2022

Related U.S. Application Data

(60) Provisional application No. 63/088,039, filed on Oct. 6, 2020.

(51) Int. Cl.
*B29C 59/16* (2006.01)
*B29C 65/08* (2006.01)

(52) U.S. Cl.
CPC ............ *B29C 59/165* (2013.01); *B29C 59/16* (2013.01); *B29C 65/08* (2013.01)

(58) Field of Classification Search
CPC ....... A61F 13/62; B29C 59/165; B29C 43/46; B29C 59/16
See application file for complete search history.

(56) References Cited

U.S. PATENT DOCUMENTS

| 3,562,041 A | 2/1971 | Robertson |
| 3,733,238 A | 5/1973 | Long |
(Continued)

FOREIGN PATENT DOCUMENTS

| EP | 3481355 B1 | 5/2019 |
| EP | 3639801 B1 | 4/2020 |
(Continued)

OTHER PUBLICATIONS

PCT Search Report and Written Opinion for PCT/US2021/053299 dated Feb. 4, 2022, 13 pages.
(Continued)

*Primary Examiner* — Alison L Hindenlang
*Assistant Examiner* — Debjani Roy
(74) *Attorney, Agent, or Firm* — Daniel S. Albrecht; Sarah M. DeCristofaro

(57) ABSTRACT

Methods and systems for mechanically forming one or more surface protrusions integrally from a garment material, the one or more surface protrusions extending outwardly from a garment surface of the garment material, include pre-heating at least one selected area of the garment material; placing the at least one selected area of the garment surface that is pre-heated against a first surface of a forming die, the first surface having a plurality of openings which have a configuration and orientation corresponding with the configuration and orientation of the one or more surface protrusions of the garment material. The garment surface may be softened by application of a source of energy, at least some of the softened garment surface positioned into at least one opening of the plurality of openings.

13 Claims, 17 Drawing Sheets

(56) References Cited

U.S. PATENT DOCUMENTS

| | | |
|---|---|---|
| 4,713,132 A | 12/1987 | Abel et al. |
| 5,667,608 A | 9/1997 | Rajala et al. |
| 6,478,784 B1 | 11/2002 | Johnson et al. |
| 6,746,434 B2 | 6/2004 | Johnson et al. |
| 8,784,722 B2 | 7/2014 | Rocha |
| 10,076,162 B2 | 9/2018 | Rocha |
| 10,798,997 B2 | 10/2020 | Rocha |
| 2003/0113529 A1 | 6/2003 | Gibson et al. |
| 2003/0213548 A1* | 11/2003 | Lehrter .................. B31F 1/07 156/220 |
| 2004/0121120 A1* | 6/2004 | Gray .................. B29C 59/025 428/119 |
| 2010/0180407 A1* | 7/2010 | Rocha .................. B29C 59/04 264/444 |
| 2013/0060223 A1* | 3/2013 | Lawson .................. A61F 13/62 604/391 |
| 2014/0264996 A1* | 9/2014 | Rocha .................. B29C 59/04 264/71 |
| 2018/0050484 A1 | 2/2018 | Rocha |
| 2018/0228669 A1 | 8/2018 | Schneider et al. |
| 2020/0179184 A1 | 6/2020 | Kaiser |
| 2022/0106713 A1 | 4/2022 | Schneider et al. |

FOREIGN PATENT DOCUMENTS

| | | |
|---|---|---|
| JP | 2015182235 A * | 10/2015 |
| WO | 9903369 A1 | 1/1999 |
| WO | 0239842 A1 | 5/2002 |
| WO | 2019018721 A1 | 1/2019 |

OTHER PUBLICATIONS

All Office Actions; U.S. Appl. No. 17/493,098, filed Oct. 4, 2021.

* cited by examiner

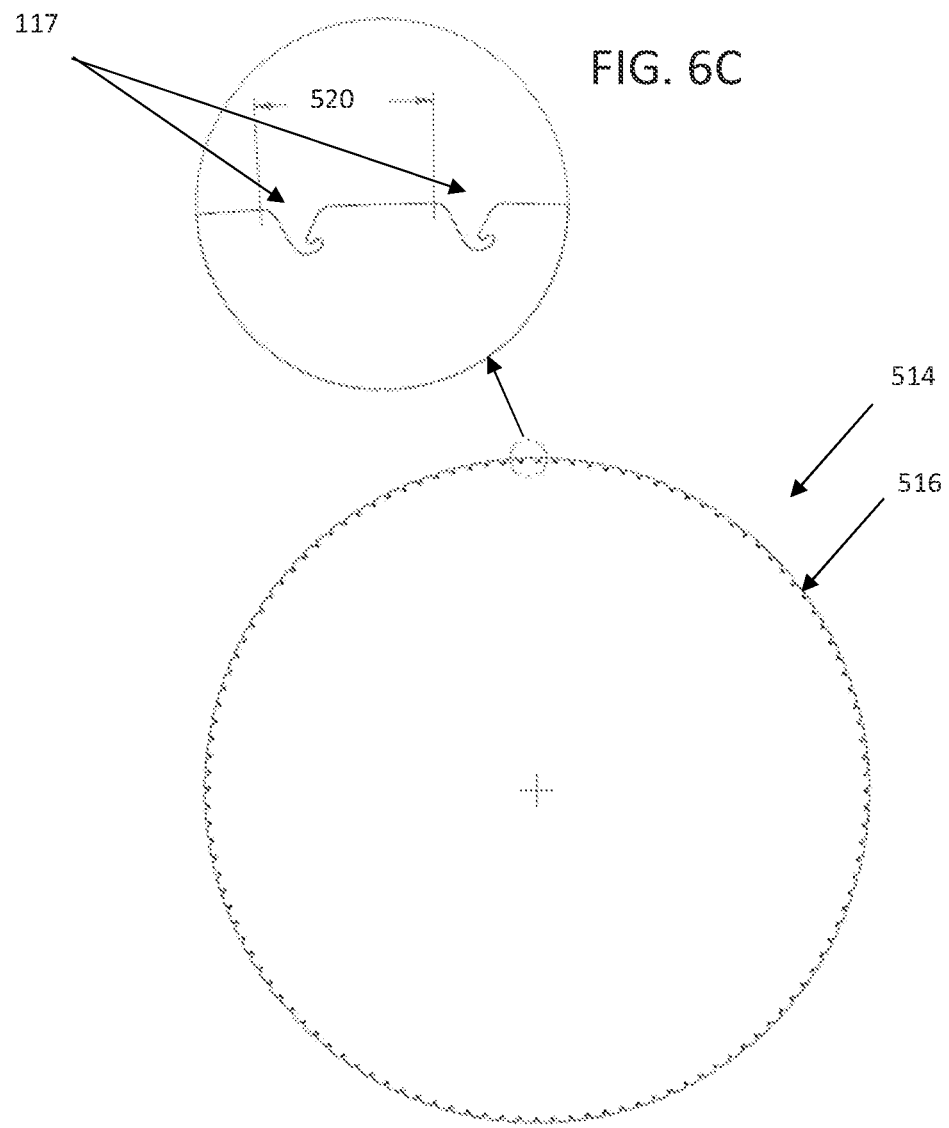

SURFACE PROTRUSION FORMATIONS AND METHODS OF MANUFACTURING

TECHNICAL FIELD

The present specification generally relates to surface protrusion formation systems and methods, and, more specifically, to systems and methods of manufacturing and forming surface protrusions on a garment, such as a diaper.

BACKGROUND

Garments, such as absorbent articles, often include fastening systems such as hook and loop fastenings systems to secure portions of the garments to one another. Such garments may include disposable diapers. Manufacturing processes may be used to form the fastening systems at a rate of throughput that manufacturers may seek to improve.

Accordingly, a need exists for alternative methods to efficiently form fastening systems, in particular fastening elements such as hooks, on a garment.

SUMMARY

The invention comprises the features of the independent claims herein. A method for mechanically forming one or more surface protrusions integrally from a garment material, the one or more surface protrusions extending outwardly from a garment surface of the garment material, comprises placing at least one selected area of the garment surface against a first surface of a forming die. The first surface has a plurality of openings which have a configuration and orientation corresponding with the configuration and orientation of the one or more surface protrusions of the garment material. The method further comprises softening the garment surface by application of a source of energy, positioning at least some of the softened garment surface into at least one opening of the plurality of openings from the first surface of the forming die, and separating the forming die from the garment surface to form the one or more surface protrusions. The source of energy comprises at least two sonotrodes mounted about a rotary drum.

A method for mechanically forming one or more surface protrusions integrally from a garment material, the one or more surface protrusions extending outwardly from a garment surface of the garment material, comprises pre-heating at least one selected area of the garment material, and placing the at least one selected area of the garment surface that is pre-heated against a first surface of a forming die. The first surface has a plurality of openings which have a configuration and orientation corresponding with the configuration and orientation of the one or more surface protrusions of the garment material. The method further comprises softening the garment surface by application of a source of energy, positioning at least some of the softened garment surface into at least one opening of the plurality of openings from the first surface of the forming die, and separating the forming die from the garment surface to form the one or more surface protrusions.

A method for mechanically forming one or more surface protrusions integrally from a garment material, the one or more surface protrusions extending outwardly from a garment surface of the garment material, comprises placing at least one selected area of the garment surface against a first surface of a forming die, the forming die having a linear form. The first surface has a plurality of openings which have a configuration and orientation corresponding with the configuration and orientation of the one or more surface protrusions of the garment material. The linear form of the forming die is disposed on a conveyor assembly. The method further comprises softening the garment surface by application of a source of energy. The source of energy includes a modular form configured for an extended contact with the linear form of the forming die when conveyed by the conveyor assembly compared to a non-modular form. The method further comprises positioning at least some of the softened garment surface into at least one opening of the plurality of openings from the first surface of the forming die, and separating the forming die from the garment surface to form the one or more surface protrusions.

A method for assembling elastic laminates and mechanically forming one or more surface protrusions integrally from a garment material, the one or more surface protrusions extending outwardly from a first surface of the garment material, comprises wrapping the first surface of a first substrate of the garment material onto an outer circumferential surface of a forming die. The forming die has a first surface having a plurality of openings which have a configuration and orientation corresponding with the configuration and orientation of the one or more surface protrusions of the garment material. The method further comprises positioning an elastic film in contact with a second surface of the first substrate on the forming die, advancing a second substrate to position a first surface of the second substrate in contact with the elastic film and the second surface of the first substrate on the forming die, and ultrasonically bonding by a source of energy the first substrate together with the second substrate with the elastic film positioned between the first substrate and the second substrate. The method further comprises softening the first surface of the first substrate by the source of energy, positioning at least some of the softened first surface into at least one opening of the plurality of openings from the first surface of the forming die, and separating the forming die from the garment material to form the one or more surface protrusions integrally from the first surface of the first substrate of the garment material.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 6B schematically illustrates a side view of a forming die including openings formed from a stacked disc configuration, according to one or more embodiments shown and described herein;

FIG. 6C schematically illustrates a detailed view of a portion of openings of the forming die of FIG. 6B;

DETAILED DESCRIPTION

Figure 1:
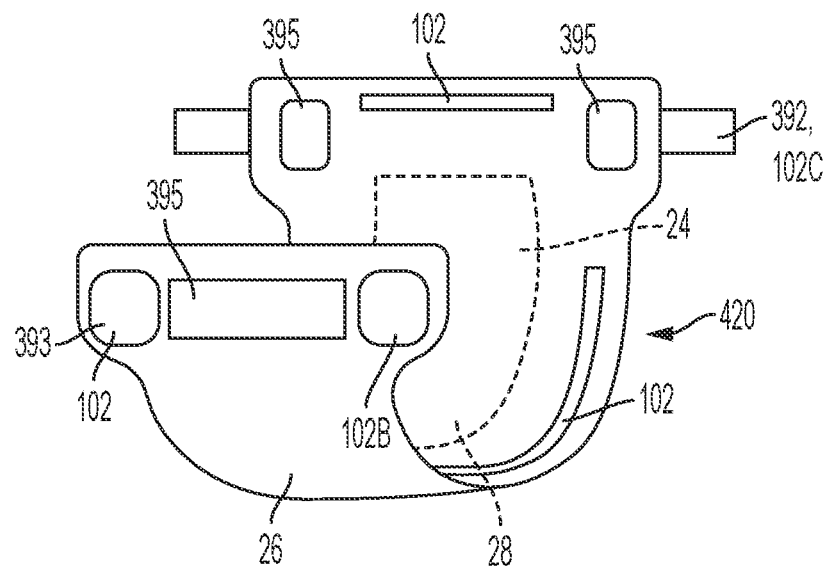
FIG. 1 schematically illustrates a garment that is a diaper, according to one or more embodiments shown and described herein.

Reference will now be made in detail to embodiments of surface protrusion formation systems and methods of manufacture, examples of which are illustrated in the accompanying drawings. Whenever possible, the same reference numerals will be used throughout the drawings to refer to the same or like parts. Various embodiments of surface protrusion formation systems will be described in further detail herein with specific reference to the appended drawings.

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

FIG. 1 generally depicts a garment material of a garment such as an absorbent article, shown in the form of a diaper 420. A portion of the garment material may be formed of a substrate, and one or more surface protrusions 102 may extend outwardly from a garment surface of the garment material. The surface protrusions 102 may provide primary fastening functions on garments, such as, for example, a diaper, a body wrap, and a sanitary napkin. The diaper 420 may include a liquid impervious topsheet 24, a liquid impervious backsheet 26, and an absorbent core 28. The diaper 420 includes a primary fastening system 392 that may include the surface protrusions 102.

In embodiments in which primary fastening systems function to maintain the absorbent article secured about the waist of the wearer, the surface protrusions 102 may be disposed on the body facing surface of the garment. The surface protrusions 102 may be disposed on the fastening tape attached to the garment.

The diaper 420 may also comprise a secondary fastening system 393 which may include surface protrusions 102 to provide a secondary anchoring about the waist and to prevent shifting of overlapped portions of the diaper 420 during use. The fastening systems described herein may include hook and loop fasteners for securing one portion of a body wrap of the diaper 420 to itself to provide primary securement of the body wrap to the wearer.

One or both of the primary and the secondary fastening systems may include other elements, such as, for example, pressure sensitive adhesives, other mechanical fasteners, or the like.

The surface protrusions 102 may also or alternatively be disposed on the outer surface of the garment in a position to maintain the garment in a disposal configuration. The surface protrusions 102 may be used with many other tape designs to secure the garment for disposal, including disposal tape systems disclosed in U.S. Pat. Nos. 6,746,434; 5,108,384; 4,869,724; 5,575,784; 5,626,573; and 5,279,604 and publications WO 98/53780 and WO 99/17693. Each of the above patents and publications is incorporated by reference herein in their entirety.

The surface protrusions 102 may be engaged with protrusion receiving zones to connect one portion of the garment to another portion of the garment. The garment may include at least one protrusion receiving zone 395, as shown in one example in FIG. 1. The protrusion receiving zone 395 provides a location at which surface protrusions 102 connect at least one portion of the garment to at least one another portion of the garment. The relative positions of surface protrusions 102 and protrusion receiving zone 395 can vary on the garment. In an embodiment, the surface protrusions 102 may be disposed on the body facing surface of the garment, and the protrusion receiving zone 395 may be disposed on the outer surface of the garment. Alternatively, the protrusion receiving zone 395 may be disposed on the body facing surface of the garment and/or the surface protrusions 102 may be disposed on the outer surface of the garment. The protrusion receiving zone 395 may be a separate piece of material added to the diaper 420 or may be an integral or monolithical part of the diaper 420, including but not limited to the topsheet 24, the backsheet 26, the leg cuff, or the waistband.

Figure 3:
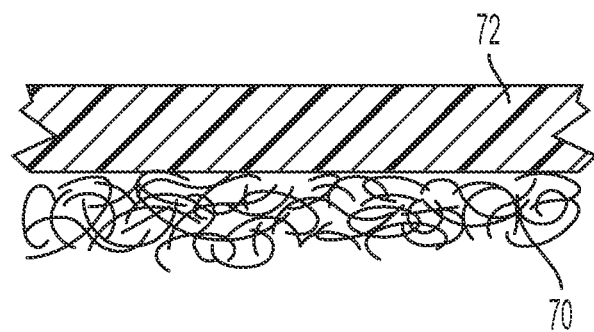
FIG. 3 schematically illustrates a non-woven material section such as of protrusion receiving zones of the diaper of FIG. 1, according to one or more embodiments shown and described herein.

The protrusion receiving zone 395 may include any suitable material that engages with the surface protrusions 102. In an embodiment, the protrusion receiving zone 395 of FIG. 1 may comprise fiber loops or at least one nonwoven layer of material. As a non-limiting example, the protrusion receiving zone 395 may include a nonwoven substrate 70 as shown in FIG. 3. Referring to FIG. 3, the nonwoven substrate 70 may be applied in overlying relationship to the outwardly-facing surface of a polymeric layer 72 to provide a plurality of loops that may define spaced open areas bounded by inter-engaged individual fibers.

The term "nonwoven" or "non-woven" refers herein to a material made from continuous (long) filaments (fibers) and/or discontinuous (short) filaments (fibers) by processes such as spunbonding, meltblowing, carding, and the like. In some configurations, a nonwoven may comprise a polyolefin based nonwoven, including but not limited to nonwovens having polypropylene fibers and/or polyethylene fibers and/or bicomponent fibers comprising a polyolefin. Nonlimiting examples of suitable fibers include spunbond, spunlaid, meltblown, spunmelt, solvent-spun, electrospun, carded, film fibrillated, melt-film fibrillated, air-laid, dry-laid, wet-laid staple fibers, and other nonwoven web materials formed in part or in whole of polymer fibers as known in the art, and workable combinations thereof. Nonwovens do not have a woven or knitted filament pattern. It is to be appreciated that nonwovens having various basis weights can be used in accordance with the methods herein. In embodiments, bicomponent fibers of the nonwoven material may include additives to be configured to more easily be susceptible to heating such as through infrared, which may aid with, for example, pre-heating or other heating of the nonwoven material as described herein.

As shown in FIG. 1, a first area including the surface protrusions 102B engage with a second area including the protrusion receiving zone 395 in inwardly adjacent the surface protrusions 102C, which may be disposed on a tape. Engaging the first area including surface protrusions 102B with the second area including the protrusion receiving zone 395 may provide a minimal resistance to peel mode disengagement and may cause an increase in friction or shear mode disengagement resistance between the portions of the garment being engaged. The surface protrusions 102 of the primary fastening system 392 of a rear waist region may engage with the protrusion receiving zone 395 of a front waist region, and the surface protrusions 102 of the secondary fastening system 393 of the front waist region may engage with the protrusion receiving zone 395 of the rear waist region.

Figure 2:
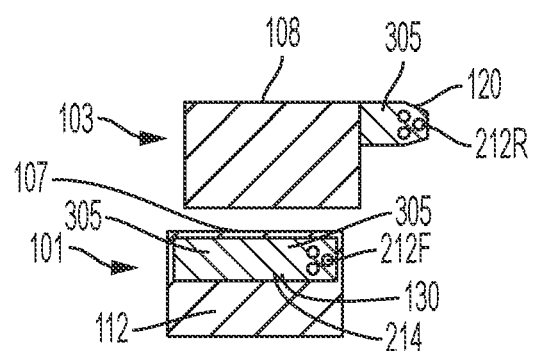
FIG. 2 schematically illustrates a hook and loop fastening system of the diaper of FIG. 1, according to one or more embodiments shown and described herein.

FIG. 2 depicts a non-limiting example of a configuration of features for diapers with hook-and-loop fastening systems. A disposable diaper such as the diaper 420 may include, as shown in FIG. 2, a front waist region 101, a rear waist region 103, a front waist edge 107, and a rear waist edge 108. A liquid-impermeable backsheet 112 may form the liquid impervious backsheet 26 of the diaper 420 and a large portion of the outward-facing surfaces. The front waist region 101 may include a landing zone 130 formed by, or including, a section of web material 214 on which one or more areas of hooks 212F of the surface protrusions 102 are integrally molded. The section of web material 214 may be adapted to serve as a section of loops material 305 with a pattern of bonds so as to fastenably engage with areas or patches of hooks 212R attached to or integrally molded on fastening members 120. The fastening members 120 may similarly be formed at least in part of a section of web material adapted to serve as the loops material 305 to fastenably engage with hooks 212F. In such a configuration, two pairs of hook-and-loop combinations engage each other as fastening pairs.

Figure 4A:
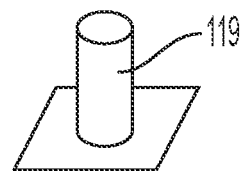
FIG. 4A schematically illustrates an embodiment of a projection of a surface protrusion, according to one or more embodiments shown and described herein.
Figure 4B:
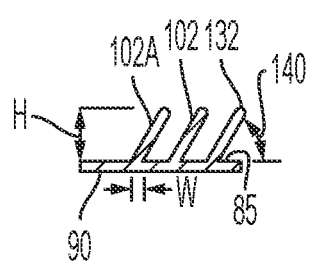
FIG. 4B schematically illustrates an embodiment of surface protrusions that are angled, according to one or more embodiments shown and described herein.
Figure 4C:
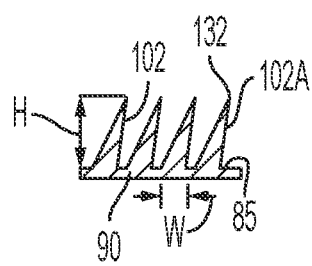
FIG. 4C schematically illustrates another embodiment of surface protrusions that are angled, according to one or more embodiments shown and described herein.
Figure 4D:
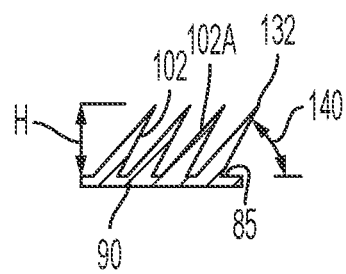
FIG. 4D schematically illustrates yet another embodiment of surface protrusions that are angled, according to one or more embodiments shown and described herein.
Figure 4E:
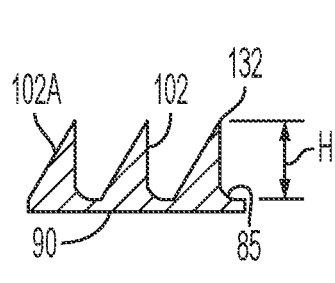
FIG. 4E schematically illustrates one other embodiment of surface protrusions that are angled, according to one or more embodiments shown and described herein.
Figure 4F:
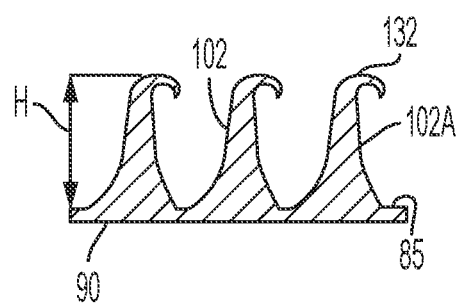
FIG. 4F schematically illustrates an embodiment of surface protrusions with a distal curved hook end, according to one or more embodiments shown and described herein.
Figure 4G:
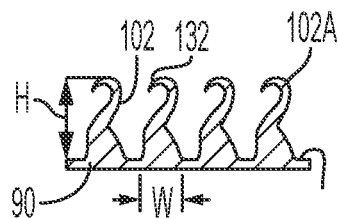
FIG. 4G schematically illustrates another embodiment of surface protrusions with a distal curved hook end, according to one or more embodiments shown and described herein.
Figure 4H:
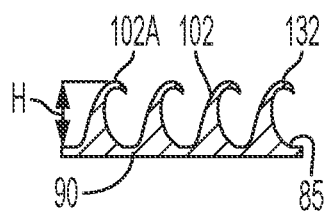
FIG. 4H schematically illustrates yet another embodiment of surface protrusions with a distal curved hook end, according to one or more embodiments shown and described herein.

Referring to FIGS. 4A-4H, the surface protrusions 102 may have one or more of a cross-sectional configuration, a height, a width, a length, an angular inclination, and a hook end configuration. The one or more surface protrusions 102 may be hooks formed normal to or at angle with respect to a garment surface of a garment material. Further, the one or more surface protrusions 102 as described herein may be of various modifiable configurations in any directionality of the hook end with respect to the garment surface, such as a left, right, angled, curved, or straight up direction. A surface protrusion 102 may be a projection 119 that is normal to the garment surface as shown in FIG. 4A. The cross-sectional configuration of surface protrusions 102 in FIGS. 4B-4H is shown as a sectional view taken generally perpendicular to a surface 85 of a garment material 90 so as to divide an individual surface protrusion 102A into equal halves, extending generally parallel to a direction defined by a projection of an individual surface protrusion 102A on surface 85. A further cross-sectional configuration of the surface protrusions 102 is a sectional view taken generally parallel to the surface 85 of the garment material 90. The further cross-sectional configuration may be of any configuration, for example, a circle, an ellipse, an oval, a triangle, a square, a rectangle, an elongated rectangle and a polygonal. The further cross-sectional configuration can be substantially consistent dimension-wise throughout the height H of the individual surface protrusion 102A, or it can be substantially tapered by being larger at the surface of the garment material 90.

The height H of surface protrusions 102 is the distance taken generally perpendicular between the surface 85 of the garment material 90 and the highest point of the individual surface protrusion 102A extending above the surface 85. The width W of the surface protrusions 102 is taken from the base of the individual surface protrusion 102A in a direction defined by a projection of the individual surface protrusion 102A on the surface 85 of the garment material 90. An angular inclination 140 of the surface protrusions 102 may be relative to the surface 85 of the garment material 90. Distal end forms 132 of the surface protrusions 102 may have various configurations as illustrated by the non-limiting examples of FIGS. 4B-4H.

Figure 5:
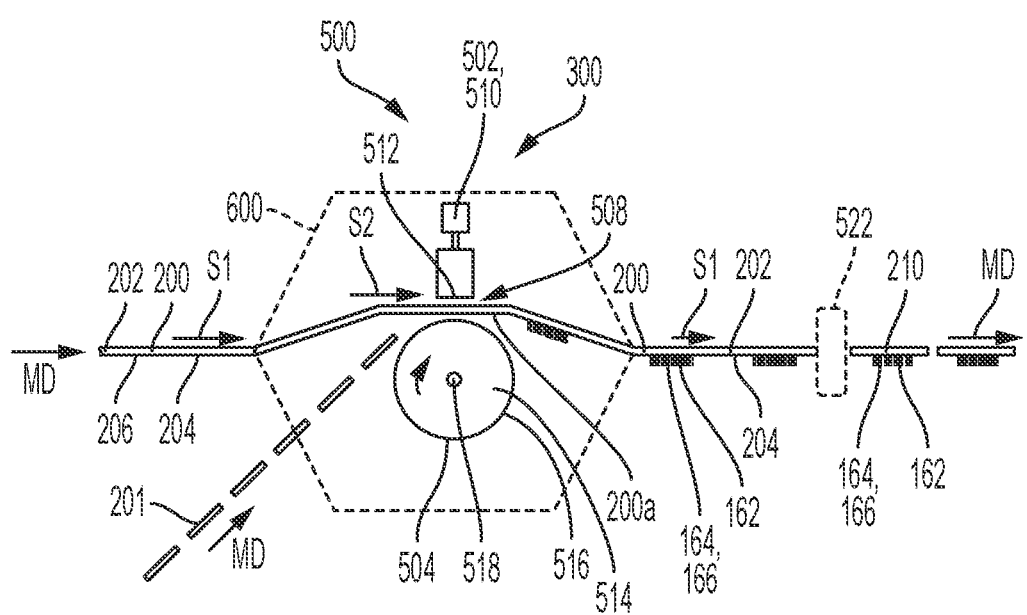
FIG. 5 schematically illustrates a side view of an apparatus for forming protrusions on an advancing substrate, according to one or more embodiments shown and described herein.

Referring to FIG. 5, a schematic side view of an apparatus for forming protrusions on an advancing substrate is shown. As shown in FIG. 5, a continuous substrate 200 may advance in a machine direction (MD) adjacent a protrusion forming apparatus or system 500 that is configured to form discrete zones 162 of first body parts 164 and distal hook ends 166 at respective distal ends 165 on the substrate 200. The substrate may comprise polymeric material. The substrate may comprise a nonwoven, a film or combinations thereof. In nonlimiting examples, the substrate comprises a nonwoven. In particular, the protrusion forming apparatus or system 500 includes energy source 502 and a die surface 504. The energy source 502 applies energy to the advancing substrate 200 such that softened material of the substrate 200 may be pressed or otherwise move or flow into the openings (e.g., cavities 117) of the die surface 504 to form a zone 162 of surface protrusions 102, 164, 166. In turn, the surface protrusions 102 are formed directly from and integrally with the material of the substrate 200. It is to be appreciated that various configurations of protrusion forming systems 500 may be used to integrally mold surface protrusions 102 directly on a substrate 200, wherein the substrate material may serve not only as a structural component material for other purposes, but also as a source of material, such as a polymer for example, for formation of the surface protrusions 102.

Figure 8:
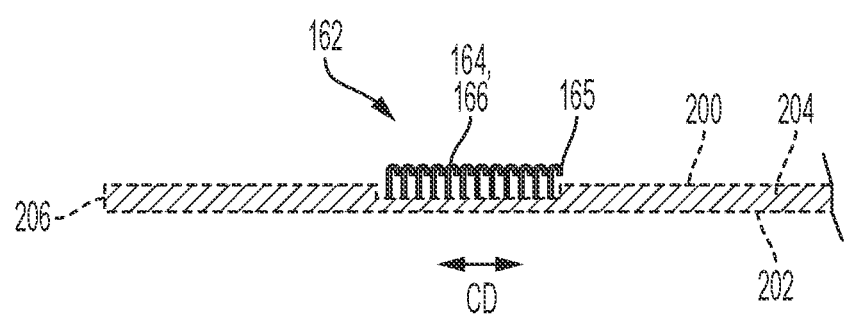
FIG. 8 schematically illustrates is a cross-sectional view of an advancing substrate showing a discrete zone of protrusions, according to one or more embodiments shown and described herein.

The substrate 200 may advance through a nip 508 between the energy source 502 and the die surface 504. As shown in FIG. 8, the substrate 200 may also define a width extending in the cross direction CD between longitudinal side edges 206. Referring again to FIG. 5, before, during, or after forming the discrete zones 162 of surface protrusions 102, it is to be appreciated that the substrate 200 may be subjected to additional manufacturing operations, such as combining, bonding, printing, cutting and/or folding operations. The substrate 200 with the protrusions formed thereon may advance to a cutter apparatus that separates the continuous substrate 200 into separate pieces 210 as discrete parts of the substrate 200. In other configurations, an apparatus assembly 300 including the system 500 may be configured with one or more bonding devices adapted to bond substrates 200, 201, including a first substrate 200 and a second substrate 201, together with an applied adhesive, pressure, heat, and combinations thereof and/or other suitable bonding techniques. In embodiments, the substrate 200 may advance through an accumulator apparatus 600 that decelerates a portion 200a of the substrate 200 to a second speed S2 less than a first speed S1. The processing lines of the apparatus assembly 300 may include an accumulator apparatus 600 that decelerates a portion 200a of an advancing substrate 200 from the first speed S1 to the second speed S2 while advancing past the protrusion forming system 500.

The energy source 502 may be configured to heat and/or otherwise apply energy to soften material of the substrate 200 such that the softened material may be pressed, drawn, or otherwise moved into the cavities 117 of the die surface 504 to form the surface protrusions 102 as described herein on the substrate 200. In some configurations, as the substrate 200 advances through the nip 508, heating of the polymeric material of the filaments, by application of heating energy, softens the material so that the material may be deformed and forced in the nip 508 and into the cavities 117 of the die surface 504. In some configurations, the die surface 504 may be cooled or otherwise temperature-controlled to help assure that the finished substrate 200 will advance from the nip 508 with formations of surface protrusions 102 that are stably formed and solidified. The formed surface protrusions 102 and areas thereof on the substrate 200 will be molded from and thereby physically integral with material(s) of which the substrate is formed. The zone 162 of surface protrusions 102 may approximately correspond with the arrangement and features of the cavities 117 in the die surface 504.

The energy source 502 may be configured in various ways. In embodiments, the energy source 502 may include an ultrasonic horn 510 having an energy transfer surface 512. As such, the ultrasonic horn 510 may be configured to impart ultrasonic energy to the substrate 200 advancing through the nip 508. For example, the substrate 200 may advance through the nip 508 such that the second surface 204 of the substrate 200 is arranged in facing relationship with the die surface 504. In turn, the ultrasonic horn 510 may apply energy to the first surface 202 of the substrate 200 advancing through the nip 508. Energy from the ultrasonic horn 510 softens material of the substrate 200 and such softened material moves into the cavities 117 to form surface protrusions 102 that extend outward from the second surface 204 of the substrate 200. It is to be appreciated that aspects of the ultrasonic horn 510 may be configured in various ways, such as for example linear or rotary type configurations. In some configurations, the ultrasonic horn 510 may be configured as a linear oscillating type sonotrode. In some configurations, the sonotrode may include a plurality of sonotrodes nested together in the cross direction CD.

The die surface 504 and/or the cavities 117 therein may be configured in various ways. For example, the protrusion forming apparatus 500 may include a roll 514 with an outer circumferential 516 surface adapted to rotate about an axis 518 of rotation. In turn, the die surface 504 may be formed to define a portion of the outer circumferential surface 516 of the roll 514. During protrusion forming operations, the substrate 200 may advance through the nip 508 with the second surface 204 in a facing relationship with the outer circumferential surface 516 of the rotating roll 514. In embodiments, the roll 514 may define various cross sectional shapes, such circular or oblong and/or may be configured to constantly or intermittently contact the substrate 200 advancing through nip 508.

Figure 6A:
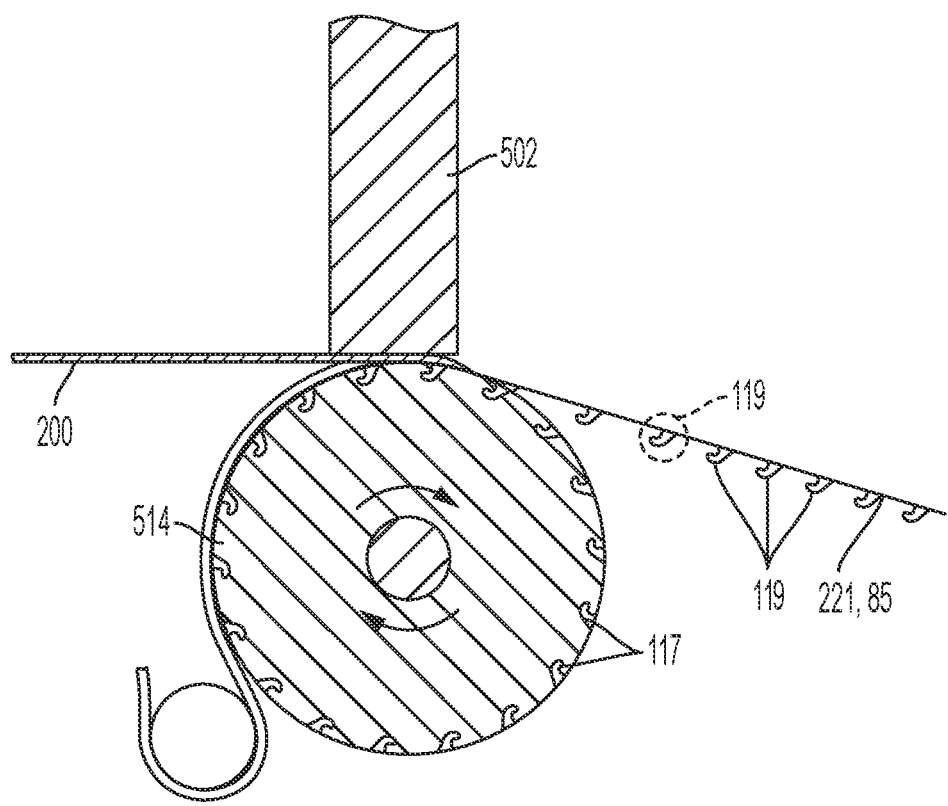
FIG. 6A schematically illustrates a cross-sectional side view of another apparatus and process for forming projections that may be used as hook-type fasteners, according to one or more embodiments shown and described herein.

Referring to FIG. 6A, a portion of a substrate 200 is a thermoplastic material substrate. The portion of the substrate 200 as referenced herein to form the one or more surface protrusions 102 includes the garment material 90 such that a referenced surface 85 of the garment material 90 is also the surface 85 of the substrate 200. The portion of the substrate 200 of FIG. 6A is in contact with the molding roll 504 and vibrating energy source 502 and may be softened by the vibration energy from the energy source 502 and a desired portion of the thermoplastic material caused to enter into one or more cavities 117 of the molding roll 504 forming hook-shaped or otherwise shaped elements or projections 119 on the surface of a substrate 221 as the roll turns in a rotary forming process. In the rotary forming process, a requisite amount of pressure may be applied to the thermoplastic material to assist in its entry and fill-out of the cavities 117. The remaining portions of the thermoplastic substrate 221 may function as a carrying strip for the hook projections 119.

FIG. 6B depicts a forming die as the roll 114 including openings as cavities 177 formed from a stacked disc configuration. FIG. 6C shows a detailed view of a portion of the openings as a pair of cavities 117 of the roll 114. The pair of cavities 117 may be spaced apart at an inclined angle 520. In an embodiment, the inclined angle may be at a 3 degrees level of inclination between initial edge portions of the pair of cavities 117.

Figure 7:
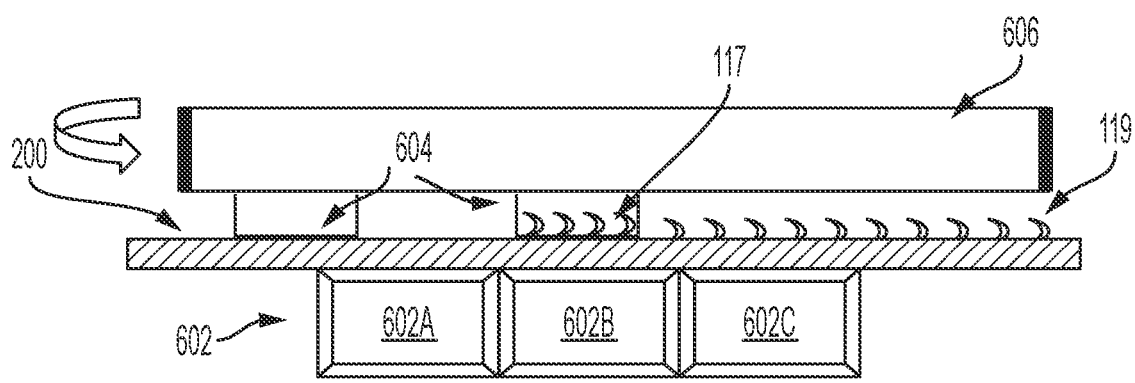
FIG. 7 schematically illustrates a side view of yet another apparatus for forming protrusions on an advancing substrate including a conveyor assembly and linear die, according to one or more embodiments shown and described herein.

Referring to FIG. 7, a side view is depicted of yet another apparatus for forming protrusions on an advancing substrate 200 including a conveyor assembly 606 and linear die as a linear molding roll 604. The conveyor assembly 606 includes and advances the linear molding roll 604 in a machine direction, and the substrate advances in a linear direction to at times be disposed between the linear molding roll 604 and an energy source 602. One or more linear molding rolls 604 may be included on the conveyor assembly 606. Each linear molding roll 604 may include the same or different configurations of the plurality of openings. As a non-limiting example, the linear molding roll 604 includes cavities 117 to form the surface protrusions 102 as projections 119 shown on the substrate 200 by use of the energy source 602. The speed of the linear molding roll may be slowed or paused when forming the surface protrusions 102. The energy source 602 may include modules 602A, 602B, and 602C. The energy source 602 may include the separate modular units to assist with maintaining a straight alignment of portions of the substrate 200 with respect to respective portions of modules 602A, 602B, and 602C of the energy source 602 during energy application to and movement of the substrate 200 in the machine direction and further allow for an extended contact time between the energy source 602 and the substrate 200.

The energy source may be configured as a sonotrode to act as a heat control loop in which a heat control system is communicatively coupled to the sonotrode. The heat control system may be configured to detect when the sonotrode is overheating above a desired temperature and/or to the cool the sonotrode, such as with ambient air. It is contemplated and within the scope of this disclosure that such heat control systems may be used with other sources of energy as described herein.

In embodiments, a forming die may be configured to provide heating, cooling, or combinations thereof. The forming die may be formed of copper, steel, or combinations thereof configured to effect such heating and/or cooling changes. Other types of materials may be used as suitable and understood to those skilled in the art to effect such heating and/or cooling changes with other thermal growth rates or capacities and/or different metallurgies to treat air resistance on the surface of the forming die. The forming die may be configured to include an exterior copper surface and a plurality of openings as cavities 117 formed of steel. In embodiments, the cavities 117 may be coated to aid with release of the formed surface protrusions 102 from respective cavities 117. The cavities and/or portions of the exterior surface could have a permanent or renewable release agent, e.g., a fluorochemical or silicone. A renewable release agent can be added continuously in the process at a low add-on level. A suitable renewable release agent is described in U.S. patent application Ser. No. 10/151,562, filed on May 20, 2002. Permanent release coatings for process components are also known to the art and typically comprise fluoropolymers or silicone resins. Additionally, or alternatively, the forming die may be configured to aid with cooling that aids in shrinkage, which helps to release the formed surface protrusions 102 with minimum or without deformation upon release.

The forming die may be configured to be heated when forming the one or more surface protrusions 102 and cooled when releasing the formed one or more surface protrusions 102. The forming die may include one or more temperature zones, such as one or more heating or cooling zones. The forming die may be configured to provide cooling through fluid such as glycol or other cooling media, air blasts, a cooling surface, or combinations thereof. In an embodiment, prior to formation of the surface protrusions 102, an infrared source may be used to heat a die surface to conduct a heated temperature into the garment material 90 disposed on the forming die to assist with reducing an amount of energy needed to soften the garment material 90 to form the protrusions 102.

In the embodiments of FIGS. 9-12, views of linear die conveyor systems 720, 730, and 740 are shown to form surface protrusions on discrete portions of a substrate 200 that are depicted as discrete substrates 722 that may be cut portions of the substrate 200. While discrete substrates 722 are shown in a standing configuration, and may be disposed around another longitudinal apparatus in the standing configuration, it is contemplated by this disclosure that the discrete substrates 722 may be disposed in a flat configuration along an assembly line prior to receipt by a linear molding roll as described herein.

Figure 9:
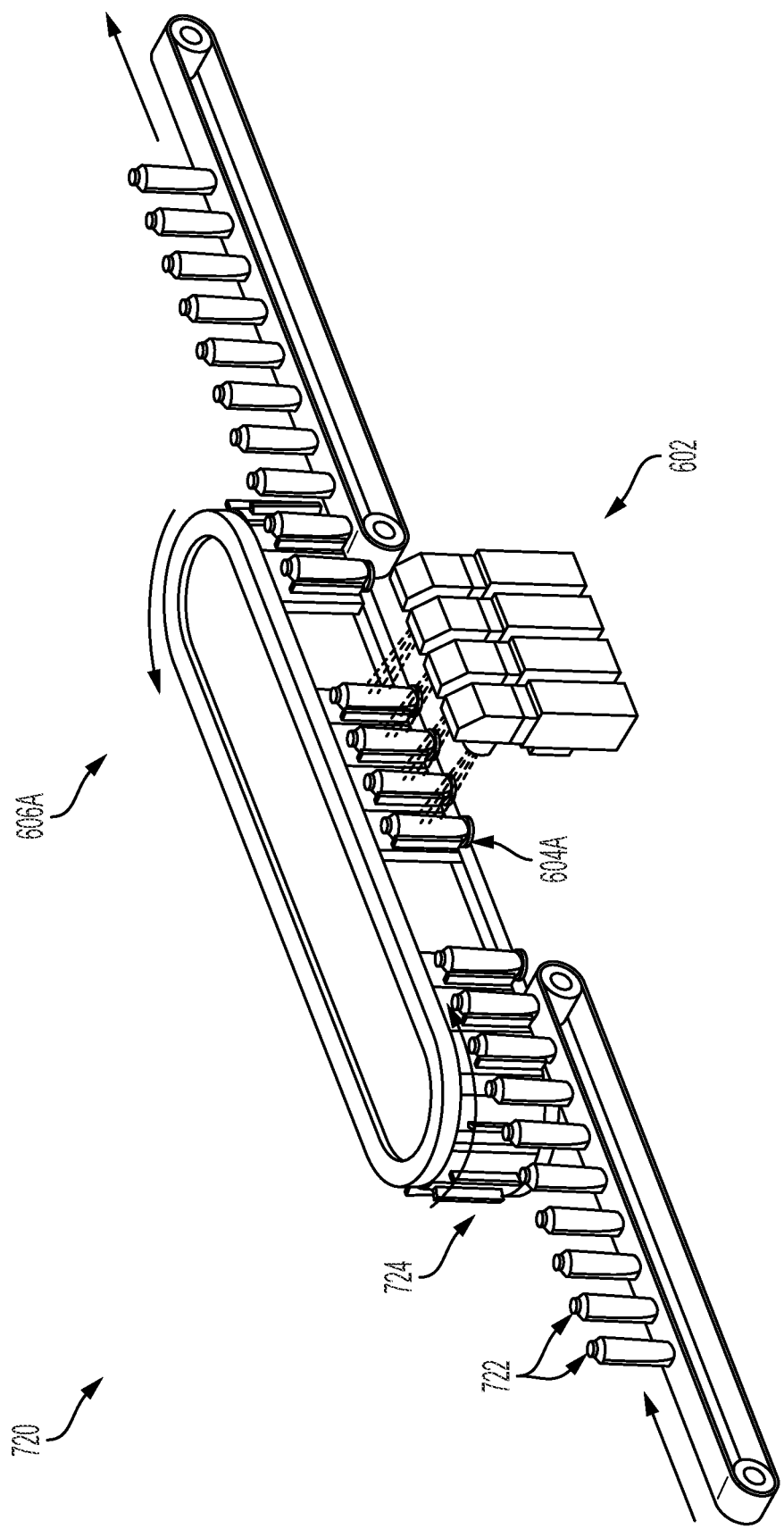
FIG. 9 schematically illustrates a side perspective view of a linear die conveyor system, according to one or more embodiments shown and described herein.

Referring to FIG. 9, a side perspective view of a linear die conveyor system 720 is shown. The linear die conveyor system 720 includes an energy source 602, a linear molding roll 604A, and a conveyor assembly 606A. The linear molding roll 604A is disposed on the conveyor assembly 606A, which moves in a rotational direction about an axis. Discrete substrates 722 as pieces of a substrate 200 advance along an assembly, such as another conveyor assembly, for receipt within respective discrete substrate receiving slots 724 of the linear molding roll 604A. At a position when the linear molding roll 604A is disposed in a facing relationship to the energy source 602, the energy source 602 is configured to soften discrete substrates 722 disposed in discrete substrate receiving slots 724 of the linear molding roll 604A. The linear molding roll 604A includes cavities to form surface protrusions 102 as described herein. The softened substrates 722 are advanced to be disposed onto another assembly, which may be another conveyor assembly, of the linear die conveyor system 720 to advance to a next stage. In an embodiment, the softened substrates 722 may be advanced to a stage at which the discrete units with the formed surface protrusions are adhesively applied to a diaper.

Figure 10:
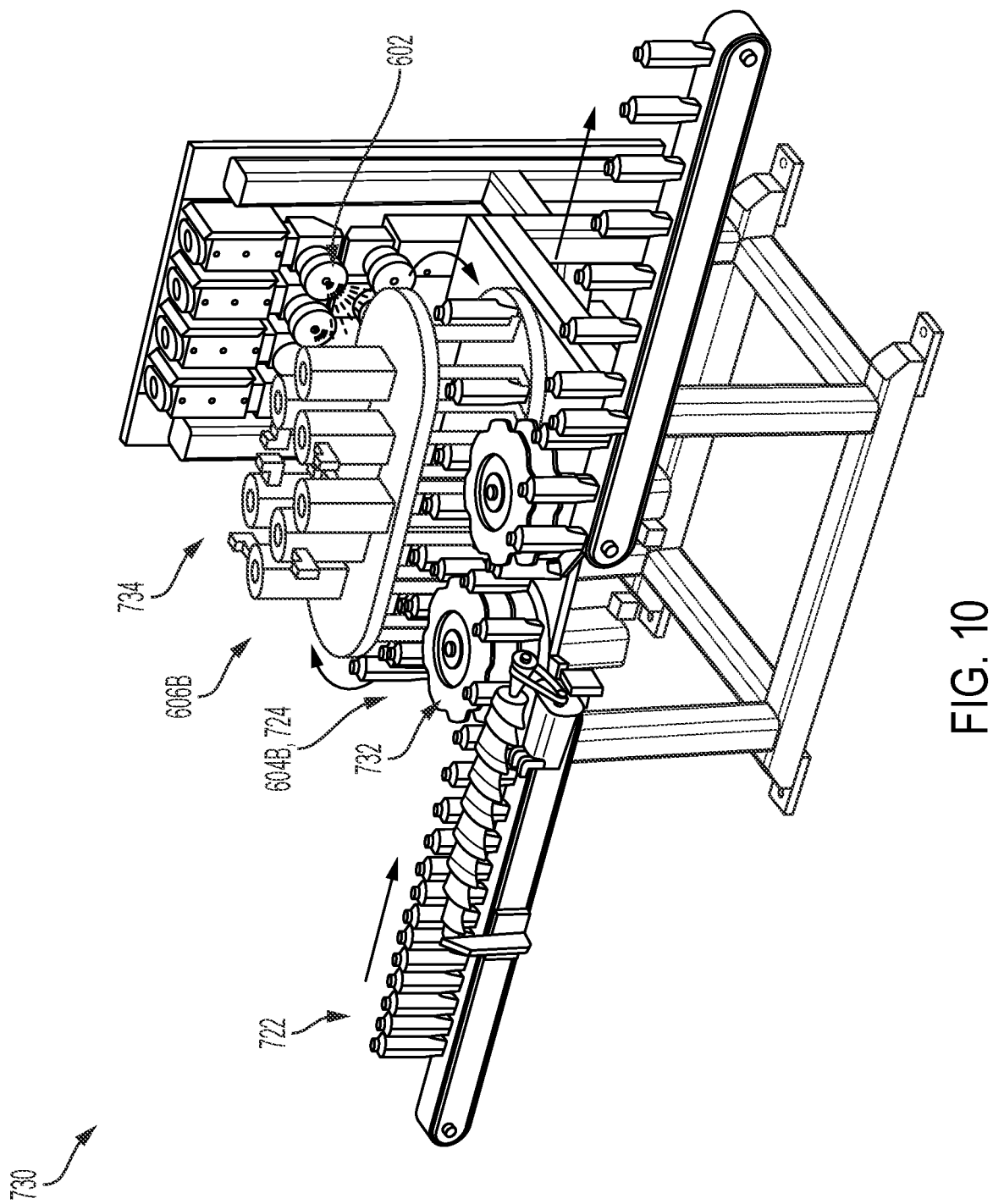
FIG. 10 schematically illustrates a side perspective view of another linear die conveyor system, according to one or more embodiments shown and described herein.
Figure 11:
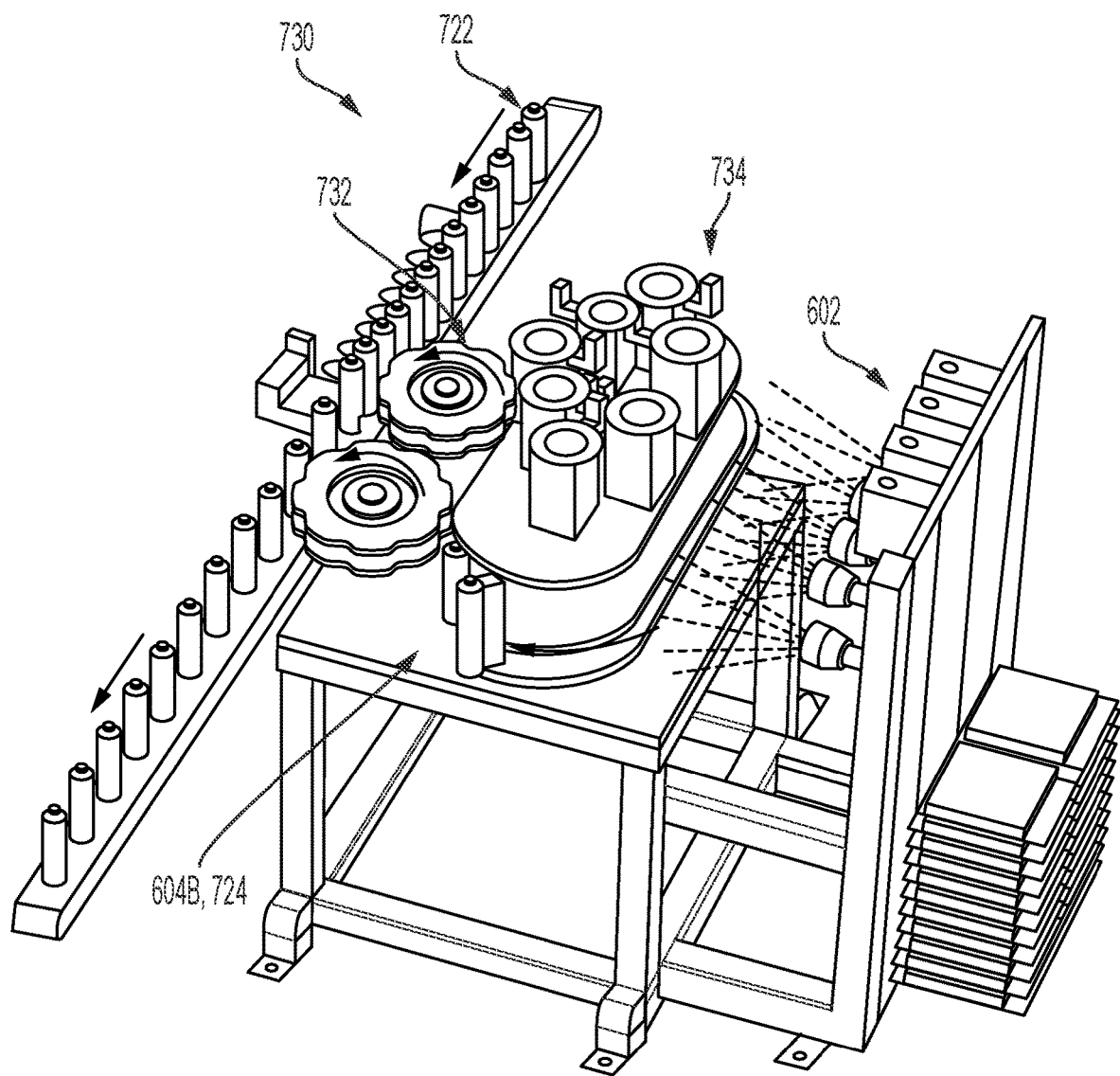
FIG. 11 schematically illustrates a rear perspective view of the linear die conveyor system of FIG. 10, according to one or more embodiments shown and described herein.

Referring to FIG. 10, a side perspective view of another linear die conveyor system 730 is shown. In FIG. 11, a rear perspective view of the linear die conveyor system 730 is shown. The linear die conveyor system 730 includes an energy source 602, a linear molding roll 604B, and a conveyor assembly 606B. The linear molding roll 604B is disposed on the conveyor assembly 606B, which moves in a rotational direction about an axis via use of a motor gear assembly 734. Discrete substrates 722 as pieces of a substrate 200 advance along an assembly, such as another conveyor assembly and rotational peg 732, for receipt within respective discrete substrate receiving slots 724 of the linear molding roll 604B. At a position when the linear molding roll 604B is disposed in a facing relationship to the energy source 602, which is shown as a rear-facing position in FIG. 11, the energy source 602 is configured to soften discrete substrates 722 disposed in discrete substrate receiving slots 724 of the linear molding roll 604B. The linear molding roll 604B includes cavities to form surface protrusions 102 as described herein. The softened substrates 722 are advanced through another rotational peg 732 and disposed onto another assembly, which may be another conveyor assembly, of the linear die conveyor system 720 to advance to a next stage.

Figure 12:
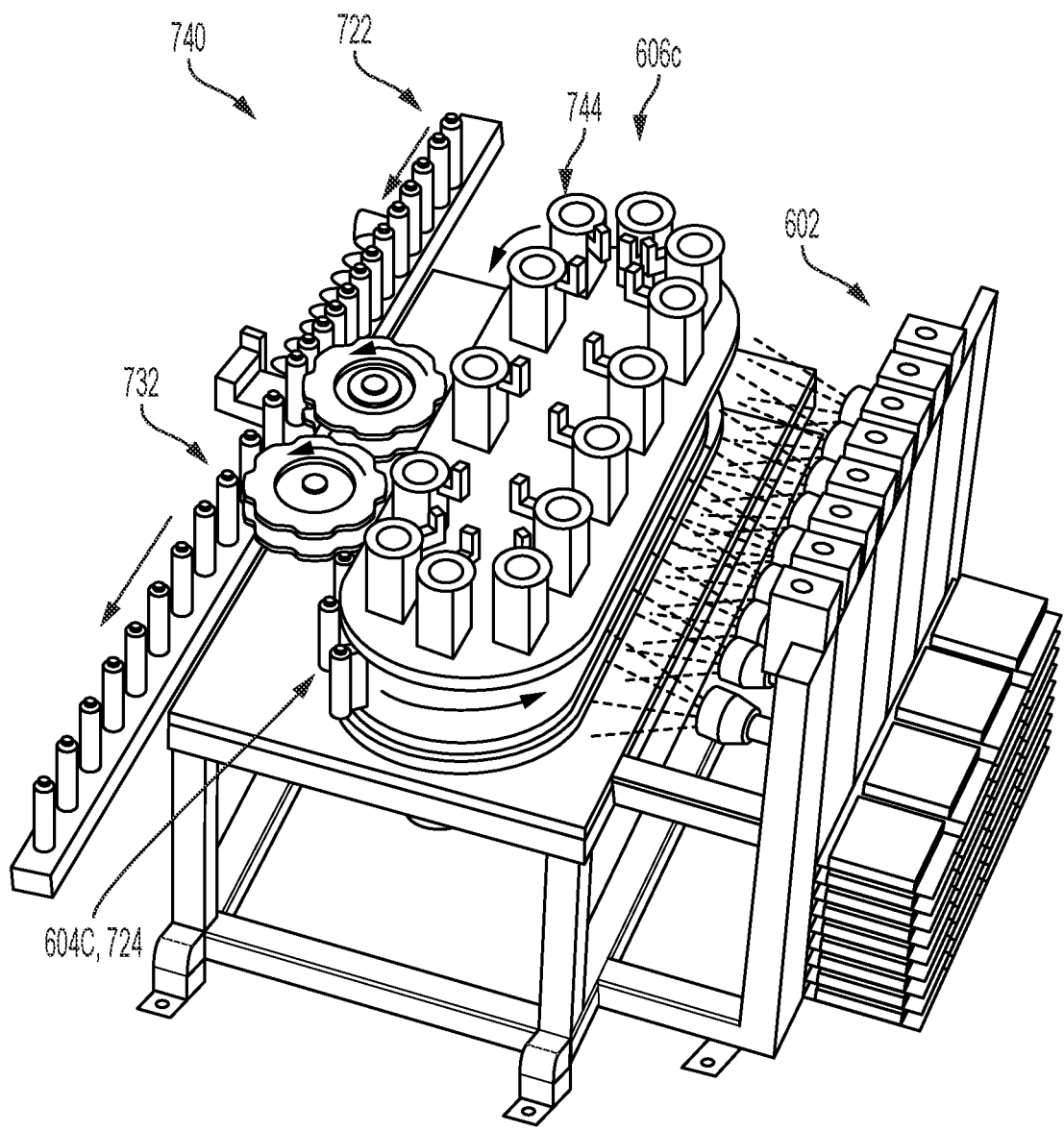
FIG. 12 schematically illustrates a rear perspective view of another linear die conveyor system, according to one or more embodiments shown and described herein.

Referring to FIG. 12, a rear perspective view of another linear die conveyor system 740 is shown. The linear die conveyor system 730 includes an energy source 602, a linear molding roll 604C, and a conveyor assembly 606C. The linear molding roll 604C is disposed on the conveyor assembly 606C, which moves in a rotational direction about an axis via use of a motor gear assembly 744. The motor gear assembly 744 includes motors arranged in a different configuration than those of the motor gear assembly 734 of FIGS. 10-11 to allow for a longer portion of a linear molding roll 604C to be exposed to a longer modular form of the energy source 602, which also aids to extend a dwell (i.e., exposure) time to soften the substrate 200. As an example, and not as a limitation, either motor gear assembly 734, 744 may be a gear assembly of a controlled motion system as set forth in U.S. Pat. No. 10,696,488, which is incorporated by referenced herein in its entirety. With respect to the linear die conveyor system 730, discrete substrates 722 as pieces of the substrate 200 advance along an assembly, such as another conveyor assembly and rotational peg 732, for receipt within respective discrete substrate receiving slots 724 of the linear molding roll 604C. At a position when the linear molding roll 604C is disposed in a facing relationship to the energy source 602, which is shown as a rear-facing position in FIG. 12, the energy source 602 is configured to soften discrete substrates 722 disposed in discrete substrate receiving slots 724 of the linear molding roll 604C. The linear molding roll 604C includes cavities to form surface protrusions 102 as described herein. The softened substrates 722 are advanced through another rotational peg 732 and disposed onto another assembly, which may be another conveyor assembly, of the linear die conveyor system 720 to advance to a next stage.

In embodiments, extended dwell time (i.e., extended contact time) between a garment material 90 of a substrate 200 and a source of energy may be achieved through a configuration of a forming die assembly as described herein, such as the linear die conveyor systems of FIGS. 9-12 and the assemblies of FIGS. 13-14 described in greater detail below. Additionally or alternatively, a sonotrode may be used as the source of energy and configured to be in a modular table form that includes a sonotrode blade or one or more block sonotrodes. Such a modular table form may be paired with a linear form of the forming die that is moving such as in the embodiment of FIG. 9 described herein. The linear form of the forming die may be configured to move through use of a linear actuator, a conveyor assembly, or the like. In an embodiment, a blade sonotrode rotated 90 degrees may include a cross-section that is aligned with a machine direction to extend dwell time between a substrate 200 on a linear forming die following the machine direction and the blade sonotrode.

Figure 13:
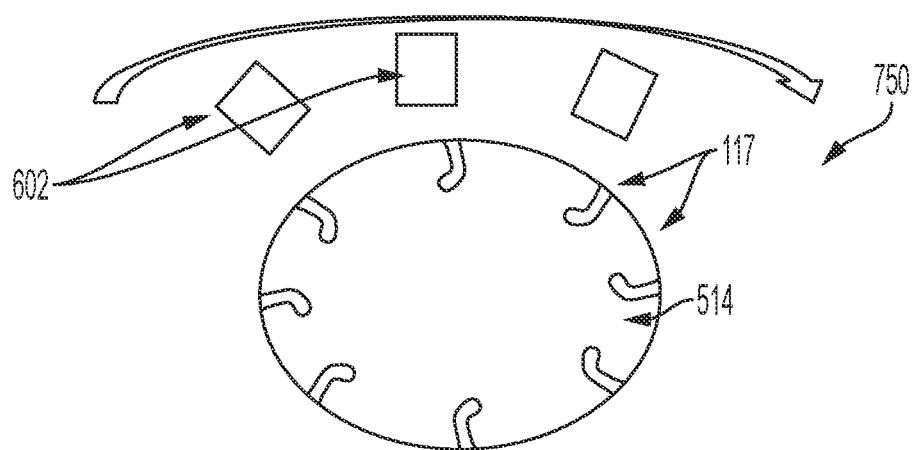
FIG. 13 schematically illustrates a side view of an apparatus and multiple energy source system for forming protrusions on an advancing substrate, according to one or more embodiments shown and described herein.
Figure 14:
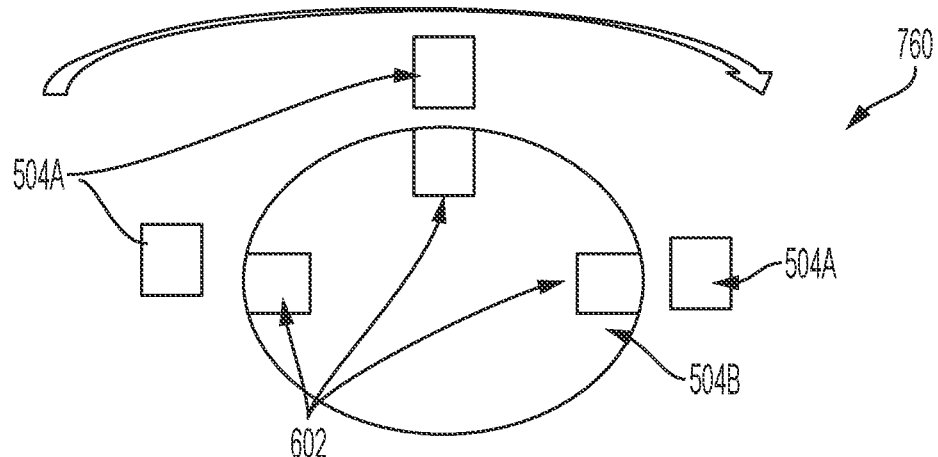
FIG. 14 schematically illustrates a side view of a multiple energy source and multiple apparatus system for forming protrusions on an advancing substrate, according to one or more embodiments shown and described herein.

FIGS. 13-14 depict another apparatus embodiments to extend a dwell time to soften a substrate 200 during the forming processes as described herein. Referring to FIG. 13, a side view of an apparatus and multiple energy source system as an extended dwell assembly 750 for forming surface protrusions 102 on an advancing substrate 200 is shown. The extended dwell assembly 750 includes a molding roll 514 that rotates in a rotational direction and includes a plurality of cavities 117 to form the surface protrusions 102 on the substrate 200 when exposed to one or more energy sources 602 as described herein. By utilizing a plurality of energy sources 602, a dwell time to form the surface protrusions 102 on the substrate 200 is extended more than through use of one of the energy sources 602 alone. Thus, the rotary forming die of FIG. 13 as the molding roll 514 may be a multi-hit system having multiple applications of energy from the multiple sonotrodes as the energy sources 602 applied in multiple steps to form the one or more surface protrusions 102 increasingly more at each of the multiple steps (e.g., positioning the material into a cavity 117 more at each step). The multiple sonotrodes are static relative to the molding roll 514, and the substrate 200 is placed onto the molding roll 514 to received applied energy in sequential energy stations. At least two sonotrodes may be static relative to the forming die. In an embodiment, a sonotrode may be a rotary sonotrode while being static relative to a position with respective to the molding roll 514.

Referring to FIG. 14, a side view of a multiple energy source and multiple apparatus system as an extended dwell assembly 760 for forming surface protrusions 102 on an advancing substrate 200 is shown. The extended dwell assembly 760 includes one or more anvils 504A that may be molding dies including cavities 117 to form surface protrusions 102 on the substrate 200. The extended dwell assembly further includes a rotary drum 504B and one or more energy sources 602. The rotary drum 504B rotates in a rotational direction about an axis. Each anvil 504A may be disposed in a fixed position and held in the fixed position with respect to the rotary drum 504B by an arm mechanism. The one or more energy sources 602 are disposed around and attached to the rotary drum 504B. Each energy source 602 is disposed in a configured aligned with a respective anvil 504A. By utilizing a plurality of energy sources 602 and a corresponding plurality of anvils 504A, a dwell time to form the surface protrusions 102 on the substrate 200 is extended than through use of one of the energy sources 602 and paired anvil 504A alone. The rotary drum 504B may act as a multi-station drum with energy sources disposed close together with the substrate 200 traveling with the anvils 504A. Sonotrodes as the energy sources 602 may be mounted within the rotary drum 504B while an arm extends from the rotary drum 504B to attach to an anvil 504A and compress the substrate 200 between the anvil 504A and the rotary drum 504B. A higher dwell time is achieved as the sonotrode maintains contact with the anvil 504A while the rotary drum 504B is rotating.

Figure 15:
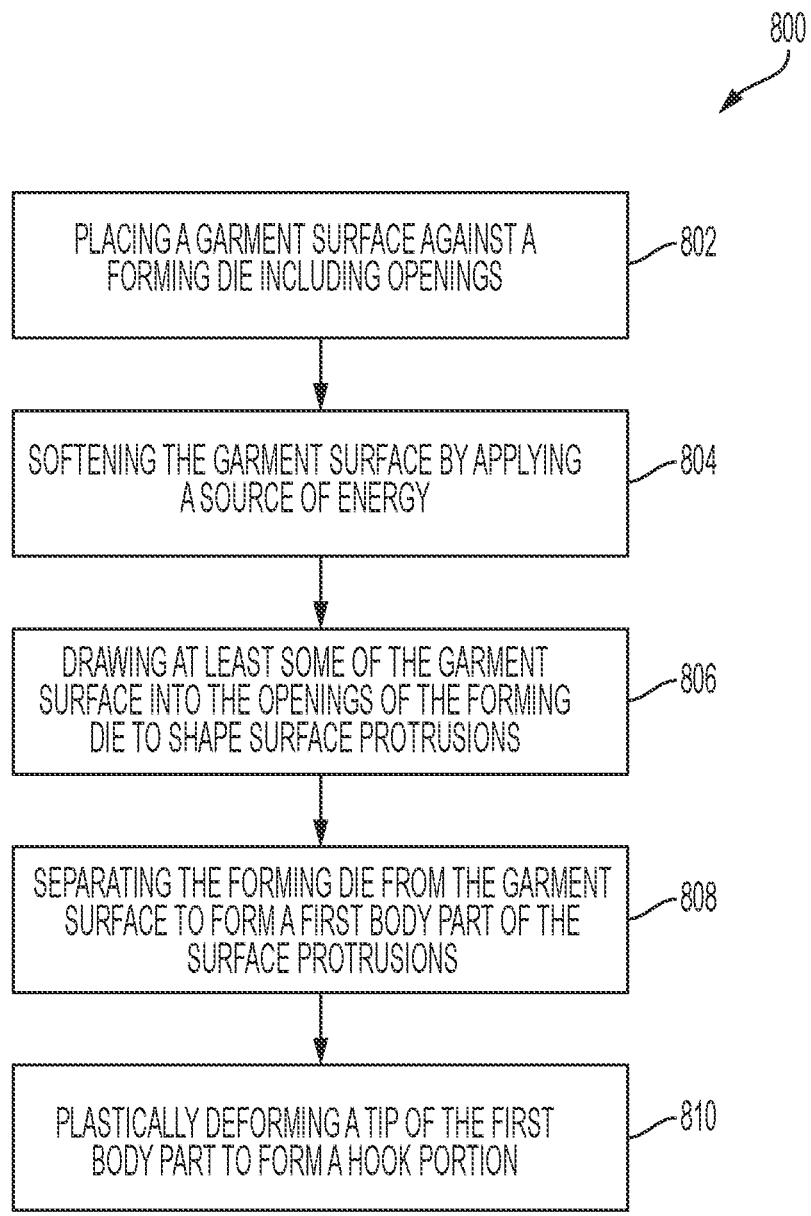
FIG. 15 schematically illustrates a two-part process for forming surface protrusions, according to one or more embodiments shown and described herein.

Referring to FIG. 15, a two-part process 800 for forming surface protrusions 102 including a separate tip deformation process is depicted as a method for mechanically forming one or more surface protrusions 102 integrally from a garment material 90 such as for the diaper 420 of FIG. 1. The garment material 90 may include a diaper that includes a loops material section (e.g., loops material 305 of FIG. 2), and the one or more surface protrusions 102 may include an array of hooks (e.g., hooks 212R, 212F of FIG. 2) configured to fasten to the loops material section as described herein. As shown in FIGS. 4A-4H, the one or more surface protrusions 102 extend outwardly from a garment surface 85 of the garment material 90.

In block 802, a garment surface of the substrate 200 is placed against a forming die. The forming die may be any of the forming die assemblies that include openings such as cavities 117 as described herein. Thus, the method includes placing at least one selected area of the garment surface 85 against a first surface (e.g., die surface 504) of a forming die. The garment surface 85 may include a polymeric material, such as a section of nonwoven web material that includes filaments of polymeric material. The forming die may be any of the forming dies as described herein and may have the first surface and a second surface opposed to the first surface. The first surface includes a plurality of openings (e.g., cavities 117) which have a configuration and orientation corresponding with the configuration and orientation of a first body part 164 of the one or more surface protrusions 102 of the garment material 90. The configuration of the plurality of openings may include a circle, an ellipse, an oval, a triangle, a rectangle, an extended rectangle, a polygon, a bore, a slot, or combinations thereof.

In a non-limiting example, the plurality of openings are formed from a stacked disc configuration of the forming die. Such a stacked disc configuration may be formed from a stacked disc concentric axial design (e.g., as shown in FIGS. 6B-6C) to fabricate the openings (e.g., cavities 117) of the forming dies described herein instead of or in addition to using alternative machining methods. The stacked disc configuration may include multiple layers respectively machined to form opening portions and/or channels and configured to be fastened together to form one or more forming dies as described herein. In some embodiments, the plurality of openings may be formed from a segmented configuration that may include fastening multiple pieces together to form the forming die via one or more fastening mechanisms. Such fastening mechanisms may include mechanical fasteners, threaded components, clamps, and the like. The segmented and/or stacked disk configurations described herein may be used to form a forming die of the embodiments described herein.

In block 804, the garment surface 85 may be softened by application of a source of energy from an energy source 502, 602 as described herein. In embodiments, the source of energy may include induction heating, ultrasonic vibrations, micro waves, radio waves, infrared waves, a laser beam, an electron beam, or combinations thereof. The one or more surface protrusions 102 may include hooks, and the garment material 90 including the garment surface 85 may include a nonwoven material. The source of energy may include an ultrasonic horn, a linear horn, a rotary horn, or combinations thereof, and the first surface of the forming die may include an outer circumferential surface of a roll that may be configured for rotation at a variable angular velocity, constant angular velocity, or combinations thereof. In an embodiment, and as shown in FIG. 13, the source of energy may include one or more sonotrodes 602, and the forming die may include a rotary form 514. In another embodiment, and as shown in FIG. 14, the source of energy may include one or more sonotrodes 602 mounted in a rotary drum 504B, and the forming die comprises one or more anvils 504A disposed about the rotary drum 504B.

In block 806 of FIG. 15, at least some of the garment surface 85 may be positioned into the openings of the forming die to shape the surface protrusions 102 as described herein. At least some of the softened garment surface 85 may be positioned into at least one opening as a cavity 117 of the plurality of openings from the first surface of the forming die. Such positioning as described herein may include drawing the softened garment surface 85 into a respective opening (e.g., cavity 117). In an embodiment, the drawing may occur through use of a vacuum process to draw a portion of the garment surface 85 into the respective opening through a negative pressure suctioning effect by use of a vacuum mechanism interacting with the openings.

In block 808, the forming die may be separated from the garment surface 85 to form the first body part 164 (FIGS. 5 and 8) of the one or more surface protrusions 102. In block 810, a tip of the first body part 164 may be plastically deformed to form a hook portion such as the hook ends 166 at distal ends 165 of the first body part 164 of the surface protrusions 102. Thus, the tip of and at a distal end 165 of the first body part 164 may be plastically deformed to the hook portion that is distal to the first body part 164 of the one or more surface protrusions 102. In block 810, the tip may be plastically deformed through a re-heating process, a capping process to force a structural change, or combinations thereof. Heat may be applied through fluid such as air, conductive surfaces, or combinations thereof.

Figure 16:
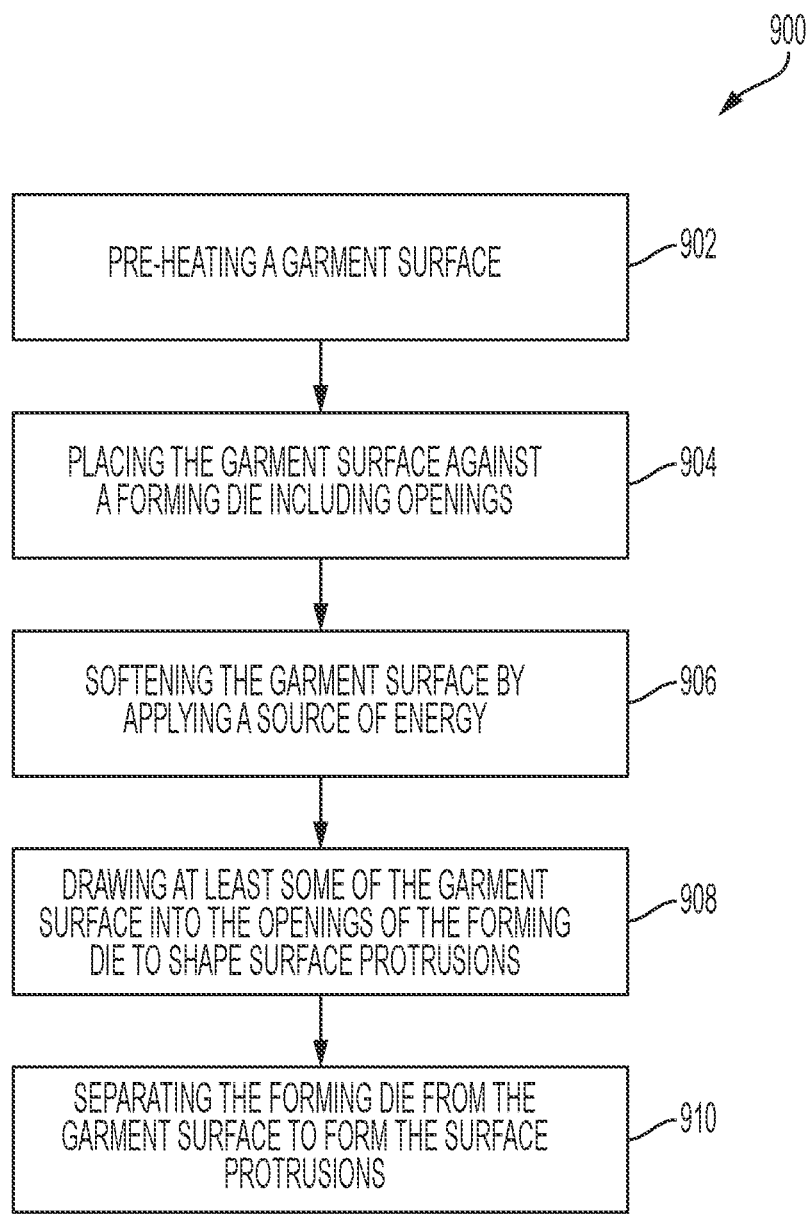
FIG. 16 schematically illustrates another two-part process for forming surface protrusions, according to one or more embodiments shown and described herein.

Referring to FIG. 16, another two-part process 900 for forming surface protrusions 102 including a pre-heating prior to forming process is depicted as a method for mechanically forming one or more surface protrusions 102 integrally from a garment material 90 such as for the diaper 420 of FIG. 1. As shown in FIGS. 4A-4H, the one or more surface protrusions 102 extend outwardly from the garment surface 85 of the garment material 90. The garment material 90 may be a diaper that includes a loops material section (e.g., loops material 305 of FIG. 2), and the one or more surface protrusions 102 may include an array of hooks (e.g., hooks 212R, 212F of FIG. 2) configured to fasten to the loops material section.

In block 902, a garment surface 85 of the substrate 200 is pre-heated. Heat may be applied through fluid such as air including convection heat (i.e., moving preheated air), radiation, conductive surfaces, energy sources such as ultrasonic energy sources, or combinations thereof. The garment surface 85 may include polymeric material, such as a section of nonwoven web material that includes filaments of polymeric material. In embodiments, the one or more surface protrusions 102 include hooks, the garment material 90 includes a nonwoven material, the source of energy may include an ultrasonic horn, a linear horn, a rotary horn, or combinations thereof, and the first surface of the forming die may include an outer circumferential surface of a roll. The roll may be configured for rotation at a variable angular velocity, at a constant angular velocity, or combinations thereof.

In block 904, the garment surface 85 of the substrate 200 that is pre-heated is placed against a forming die. The forming die may be any of the forming die assemblies that include openings such as cavities 117 as described herein. The configuration of the plurality of openings may include a circle, an ellipse, an oval, a triangle, a rectangle, an extended rectangle, a polygon, a bore, a slot, or combinations thereof. The plurality of openings may be formed from a stacked disk configuration of the forming die.

In block 906, the garment surface 85 may be softened by applying a source of energy from an energy source 502, 602 as described herein. As the garment surface 85 has been pre-heated, less energy is required from the source of energy to soften the garment surface 85 to a desired amount to form the surface protrusions 102 as described herein. The source of energy may include induction heating, ultrasonic vibrations, micro waves, radio waves, infrared waves, a laser beam, an electron beam, or combinations thereof. Thus, when the source of energy includes ultrasonic vibrations, less ultrasonic energy is required when the garment surface 85 has been pre-heated when forming the surface protrusions 102. The source of energy may include one or more sonotrodes, and the forming die may include a rotary form. As shown in FIG. 14, the source of energy may include one or more sonotrodes 602 mounted in a rotary drum 504B, and the forming die may include one or more anvils 504A disposed about the rotary drum 504B.

In block 908 of FIG. 16, at least some of the garment surface 85 may be positioned into the openings such as cavities 117 of the forming die to shape the surface protrusions 102 as described herein. In block 910, the forming die may be separated from the garment surface 85 to form the surface protrusions 102.

Figure 17:
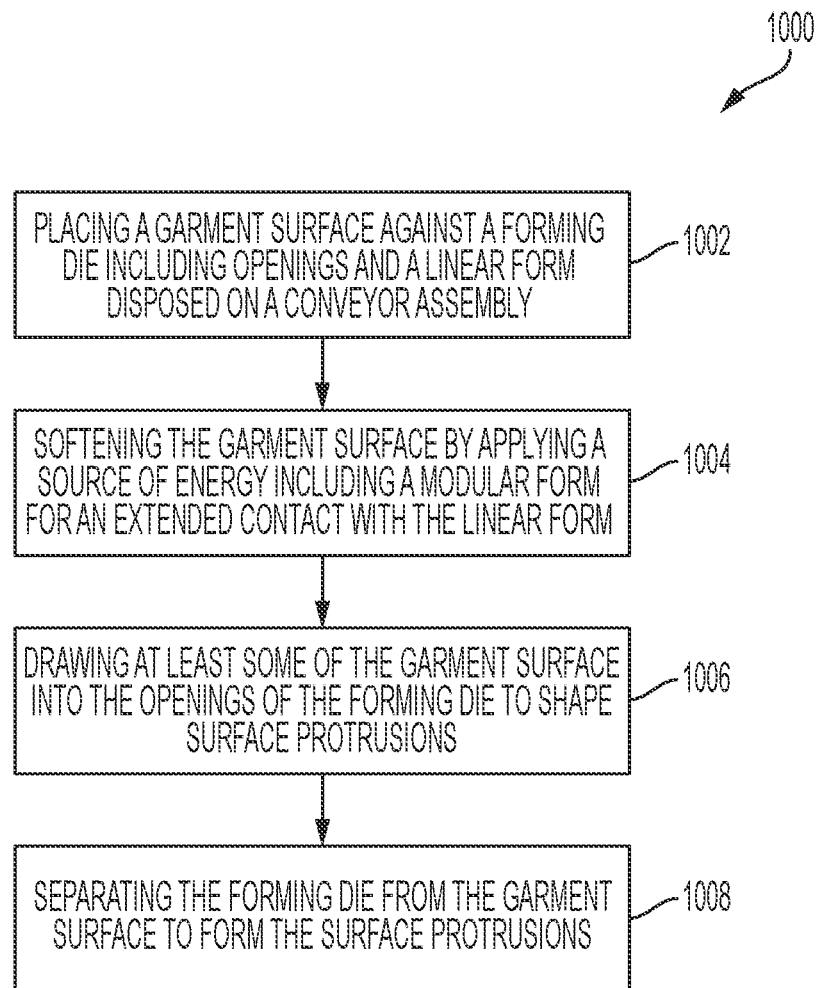
FIG. 17 schematically illustrates an extended contact process for forming surface protrusions, according to one or more embodiments shown and described herein.

Referring to FIG. 17, an extended contact process 1000 for forming surface protrusions 102 is depicted as a method for mechanically forming one or more surface protrusions 102 integrally from a garment material 90 such as for the diaper 420 of FIG. 1. As shown in FIGS. 4A-4H, the one or more surface protrusions 102 extend outwardly from the garment surface 85 of the garment material 90.

In block 1002, a garment surface 85 of the substrate 200 is placed against a forming die. The garment surface 85 may include polymeric material, such as a section of nonwoven web material. The garment material 90 of the garment surface 85 may be used to form a diaper having a loops material section (e.g., loops material 305 of FIG. 2), and the one or more formed surface protrusions 102 may include an array of hooks (e.g., hooks 212R, 212F of FIG. 2) configured to fasten to the loops material section. In some embodiments, the loops material section may include a plurality of loops, and at least a portion of the plurality of loops may be integrally formed from the section of nonwoven web material.

The forming die may be any of the forming die assemblies that are of a linear form advanced on a conveyor assembly such as the linear die conveyor systems 720, 730, and 740 of FIGS. 9-12 and that include openings such as cavities 117 as described herein. At least one selected area of the garment surface 85 may be placed against a first surface of a forming die of a linear die conveyor system 720, 730, 740. The forming die is of a linear form and may have a second surface opposed to the first surface. The first surface has a plurality of openings (e.g., cavities 117) which have a configuration and orientation corresponding with the configuration and orientation of the one or more surface protrusions 102 of the garment material 90. The plurality of openings may provide communication between the first surface and the second surface of the forming die, such as when a vacuum is disposed at or near the second surface. The linear form of the forming die is disposed on a conveyor assembly such as shown in FIGS. 9-12.

In block 1004 of FIG. 17, the garment surface 85 may be softened by applying a source of energy from an energy source 502, 602 as described herein that may include a modular form to extend contact time with the linear form of the forming die. The garment surface 85 may be softened by application of a source of energy that includes a modular form configured for an extended contact with the linear form of the forming die when conveyed by the conveyor assembly compared to contact time using a non-modular form. The source of energy may include induction heating, ultrasonic vibrations, micro waves, radio waves, infrared waves, a laser beam, an electron beam, or combinations thereof. In embodiments, the one or more surface protrusions 102 may include at least one hook, the garment material may include a nonwoven material, and the source of energy may include an ultrasonic horn, a linear horn, or combinations thereof.

In block 1006, at least some of the garment surface 85 may be positioned into the openings such as cavities 117 of the forming die to shape the surface protrusions 102 as described herein. At least some of the softened garment surface 85 is positioned into at least one opening of the plurality of openings from the first surface of the forming die. The configuration of the plurality of openings may include a circle, an ellipse, an oval, a triangle, a rectangle, an extended rectangle, a polygon, a bore, a slot, or combinations thereof.

In block 1008, the forming die may be separated from the garment surface 85 to form the one or more surface protrusions 102. Embodiments of the formed surfaced protrusions 102 may be in various configurations such as those depicted in FIGS. 4A-4H. In an embodiment directed to festooning and affecting a speed of manufacture, separating the forming die from the garment surface 85 may occur at an infeed speed different from an outfeed speed at which the at least one selected area of the garment surface 85 is placed against the first surface of the forming die. Thus, the difference in the infeed speed and the outfeed speed causes a variable speed when the at least some of the softened garment surface 85 are being positioned into the plurality of openings. The variable speed is may be slower than the infeed speed. A first accumulator may be configured to collect a portion of the substrate 200 at the infeed speed, and a second accumulator may be configured to release a portion of the substrate 200 at the outfeed speed, and a speed variance as described herein may be utilized to slow the substrate 200 speed down in the machine direction to increase a dwell time between a forming die and a source of energy and the substrate disposed therebetween.

Figure 18:
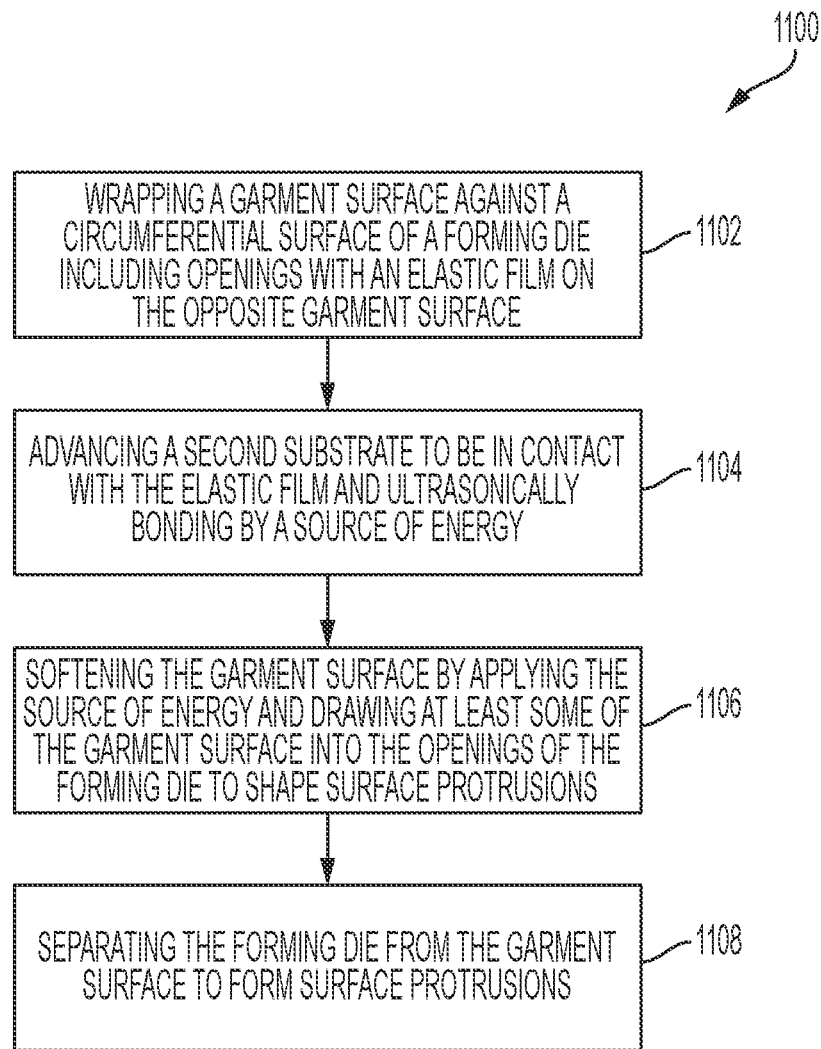
FIG. 18 schematically illustrates a process for bonding substrates and forming surface protrusions using a dual-purpose forming die, according to one or more embodiments shown and described herein.

Referring to FIG. 18, a process 1100 for bonding substrates 200, 201 and forming surface protrusions 102 using a dual-purpose forming die is depicted. An ultrasonic back ear formation bonding process as set forth in U.S. Pat. No. 10,568,776, which is incorporated by referenced herein, may be utilized. The method herein may be used for an online surface protrusion and ear formation process utilizing a single forming die for ear laminate bonding and surface protrusion formation. Thus, the same forming die and source of energy assembly may be utilized to form ultrasonic back ear patterns and surface protrusions, such as hooks. The forming die may include bonding nubs for lamination as well as openings such as cavities 117 from which to form protrusions. Bonding may be applied to one region of the material, and surface protrusions may be formed on another region of the material by the dual-purpose forming die. The method may be used to assemble laminates by a forming die and also for mechanically forming with the forming die one or more surface protrusions 102 integrally from one or more garment materials 90, such as for the diaper 420 of FIG. 1. The garment material 90 may include a section of nonwoven web material that includes filaments of polymeric material. The garment material 90 may form a diaper that includes a loops material section (e.g., loops material 305 of FIG. 2), and the one or more surface protrusions 102 may include an array of hooks (e.g., hooks 212R, 212F of FIG. 2) configured to fasten to the loops material section. As shown in FIGS. 4A-4H, the one or more surface protrusions 102 extend outwardly from a first surface (e.g., the garment surface 85) of the garment material 90.

In some embodiments, the method may utilize the forming die to assemble a laminate of two materials and form hooks on at least one of the materials. For example, two different substrates may advance through the processes on the same machine such that a first substrate is laminated to a second substrate, and the first substrate has hooks formed thereon and as described herein. As another non-limiting example, the method may utilize the forming die to assemble a laminate of two materials and to form protrusions on a third material, which may be attached to one or both of the two materials upstream or downstream of the protrusion forming process. As a further non-limiting example, two separated materials may be advanced to utilize the forming die to assemble laminates and form protrusions on at least one of the materials and the two separated materials may further downstream be bonded together when forming the diaper 420.

In block 1102, a garment surface 85 is wrapped against a circumferential surface of a forming die including openings such as cavities 117, with an elastic film disposed on the opposite garment surface (FIG. 5). The first surface of a first substrate 200 of the garment material 90 may be wrapped onto an outer circumferential surface of a forming die that has a first surface and a second surface opposed to the first surface. The first surface includes a plurality of openings (e.g., cavities 117) which have a configuration and orientation corresponding with the configuration and orientation of the one or more surface protrusions 102 of the garment material 90. The plurality of openings may provide communication between the first surface and the second surface of the forming die. The configuration of the plurality of openings may include a circle, an ellipse, an oval, a triangle, a rectangle, an extended rectangle, a polygon, a bore, a slot, or combinations thereof.

In block 1104, a second substrate 201 (FIG. 6A) is advanced to be in contact with the elastic film and ultrasonically bonded by a source of energy, such as an energy source 502, 602 as described herein. The elastic film is positioned to be in contact with a second surface of the first substrate 200 on the forming die. A second substrate 201 is advanced to position a first surface of the second substrate 201 in contact with the elastic film and the second surface of the first substrate 200 on the forming die. The source of energy is used to ultrasonically bond the first substrate 200 together with the second substrate 201 with the elastic film positioned between the first substrate 200 and the second substrate 201. In embodiments, the source of energy may include induction heating, ultrasonic vibrations, microwaves, radio waves, infrared waves, a laser beam, an electron beam, or combinations thereof. In embodiments, the one or more surface protrusions 102 include hooks, the garment material 90 includes a nonwoven material, the source of energy includes an ultrasonic horn, a linear horn, a rotary horn, or combinations thereof, and the first surface of the forming die includes an outer circumferential surface of a roll. The roll may be configured for rotation at a variable angular velocity.

The method may include advancing the elastic film to a spreader mechanism. The elastic film may include a first edge and a second edge separated from the first edge in a cross direction by a central region. The elastic film may be stretched at the spreader mechanism in the cross direction to a first elongation. The elastic film may be advanced from the spreader mechanism to the forming die. The elastic film may be consolidated to a second elongation in the cross direction. The second elongation may be less than the first elongation, and the elastic film may remain stretched in the cross direction at the second elongation. The spreader mechanism may include a ring rolling apparatus and a first disk and a second disk canted relative each other. Each disk may include an outer rim. As the first and second disks rotate, the outer rims may be separated from each other by a distance that increases from a minimum distance at a first location to a maximum distance at a second location. The elastic film may be advanced from the ring rolling apparatus to the first disk and the second disk. The elastic film may be consolidated to the second elongation by advancing the elastic film on the rotating first disk and second disk downstream of the second location.

In block 1106, the garment surface 85 is softened by applying the source of energy and positioning at least some of the garment surface 85 into the openings (e.g., cavities 117) of the forming die to shape the surface protrusions 102. For example, the first surface of the first substrate 200 is softened by the source of energy, and at least some of the softened first surface is positioned into at least one opening of the plurality of openings from the first surface of the forming die.

In block 1108, the forming die is separated from the garment surface 85 to form the surface protrusions 102 as described herein. The forming die may be separated from the garment material 90 to form the one or more surface protrusions 102 integrally from the first surface (e.g., garment surface 85) of the first substrate 200 of the garment material 90.

In any of the foregoing embodiments described herein, the material may be pretreated to facilitate the heating and/or softening of the material. In non-limiting examples, the material may be combined with receptor material and subjected to radio frequencies or microwave frequencies, which initiates a thermo, electromagnetic and/or chemical reaction. The receptor material may be combined with the garment material during formation of the garment material or via lamination. An exemplary receptor material is JPX-0512X66-41 obtained from Johnson Polymer Company. In embodiments, the section of nonwoven may be combined with a radiofrequency receptor and exposed to radioactivity. An example of such exposure is disclosed in US 2003/0113529.

In post formation of any of the forming embodiments described herein, the formed one or more surface protrusions 102 may be provided with a coating or additive to achieve a desired quality such as softness to a desired level or the like. Polymers may be applied to the protrusions via spraying or coating. Suitable polymers have lower Young's modulus values, such as elastomers and other polymers having Young's modulus values in the MPa range as compared to plastic materials that have modulus in GPa range. In another approach, sleek chemical finish can be coated on the protrusions. Chemical finishes based on oil, silicone, esters, fatty acids, surfactant etc. can be employed. Softeners such as anionic, cationic or nonionic can also be used to improve drape, and touch. Various coating techniques, like roll coating, screen coating, gravure coating, slot coating, spray coating, can be used to apply finish. For some applications, additives can be compounded with garment material forming polymers. The additives migrate to surface after protrusion formation and as the protrusions cool down. Amine and amide-based additives may be used up to 5% to impart softness. In embodiments, the one or more protrusions may be coated with a softening agent, may utilize one or more melt additives in the garment material, or combinations thereof.

Additionally, or alternatively, a radiation treatment may be applied as a curing treatment to the formed one or more surface protrusions 102 to build a strength of the formed protrusions 102 through resulting chemical crosslinking. In particular, where the garment comprises a polymeric material, the garment may be combined with commonly known radiation susceptible agents (e.g., acrylates) and treated with ultraviolent light or electron beam energy waves. When exposed to the radiation, a chemical reaction may occur, causing the modulus of the protrusion to increase, resulting in increased stiffness.

In any of the embodiments described herein, the formed one or more surface protrusions 102 may be configured to be used for registration and/or quality reference as a registration mark, quality mark, or combinations thereof. As a non-limiting example, an opacity of a patch may be determined and used to register a landing zone 130 (FIG. 1) of a product, such as a diaper 420 (FIG. 1). The characteristics of the surface protrusions 102 such as opacity may be used to register components to the product and make sure components are in correct positions. Further, opacity or other qualities of the surface protrusions 102 may be utilized for quality checks such as where a desired opacity of the surface protrusions 102 is to be achieved to obtain an acceptable quality rating.

In embodiments, the garment material 90 of the substrate 200 may be pre-treated for color. As a non-limiting example, ultraviolet (UV) light radiation may be utilized with a forming die such that a dye in the resin of the garment material 90 is configured to react to the UV light. An intensity and/or duration of the UV light may cause the reacting resin to change the color of a portion of the garment material 90 including the resin reacting to the UV light. Alternatively, or additionally, microcapsules may be embedded within the garment material 90 and crushed to release color. The sources of energy as described herein may be configured to crush the microcapsules in the garment material 90 to release the associated microcapsule color. Such color treatment embodiments may be used in addition to or alternative of external color printing.

Combinations

A. A method for mechanically forming one or more surface protrusions integrally from a garment material, the one or more surface protrusions extending outwardly from a garment surface of the garment material, the method comprising:
  i) pre-heating at least one selected area of the garment material;
  ii) placing the at least one selected area of the garment surface that is pre-heated against a first surface of a forming die, the first surface having a plurality of openings which have a configuration and orientation corresponding with the configuration and orientation of the one or more surface protrusions of the garment material;
  iii) softening the garment surface by application of a source of energy;
  iv) positioning at least some of the softened garment surface into at least one opening of the plurality of openings from the first surface of the forming die; and
  v) separating the forming die from the garment surface to form the one or more surface protrusions.

B. The method according to paragraph A, wherein the source of energy comprises induction heating, ultrasonic vibrations, micro waves, radio waves, infrared waves, a laser beam, an electron beam, or combinations thereof.

C. The method according to paragraphs A or B, wherein the configuration of the plurality of openings comprise a circle, an ellipse, an oval, a triangle, a rectangle, an extended rectangle, a polygon, a bore, a slot, or combinations thereof.

D. The method according to any of the preceding paragraphs, wherein the garment surface comprises a section of nonwoven web material, the section of nonwoven web material comprising filaments of polymeric material.

E. The method according to any of the preceding paragraphs, wherein the forming die comprises a linear form.

F. The method according to any of the preceding paragraphs, further comprising coating the one or more surface protrusions with a release agent.

G. The method according to any of the preceding paragraphs, wherein the one or more surface protrusions comprise hooks, the garment material comprises a nonwoven material, the source of energy comprises an ultrasonic horn, a linear horn, a rotary horn, or combinations thereof, and the first surface of the forming die comprises an outer circumferential surface of a roll, the roll configured for rotation at a variable angular velocity.

H. The method according to any of the preceding paragraphs, wherein the source of energy comprises one or more sonotrodes, and the forming die comprises a rotary form.

I. The method according to any of the preceding paragraphs, wherein the source of energy comprises one or more sonotrodes mounted in a rotary drum, and the forming die comprises one or more anvils disposed about the rotary drum.

J. The method according to any of the preceding paragraphs, wherein the source of energy comprises at least two sonotrodes that are static relative to the forming die.

K. The method according to any of the preceding paragraphs, further comprising treating the one or more surface protrusions with radiation for crosslinking.

L. A method for assembling by a forming die elastic laminates and mechanically forming one or more surface protrusions integrally from a garment material, the one or more surface protrusions extending outwardly from a first surface of the garment material, the method comprising:
  (i) wrapping the first surface of a first substrate of the garment material onto an outer circumferential surface of a forming die, the forming die having a first surface, the first surface having a plurality of openings which have a configuration and orientation corresponding with the configuration and orientation of the one or more surface protrusions of the garment material;
  (ii) positioning an elastic film in contact with a second surface of the first substrate on the forming die;
  (iii) advancing a second substrate to position a first surface of the second substrate in contact with the elastic film and the second surface of the first substrate on the forming die;
  (iv) ultrasonically bonding by a source of energy the first substrate together with the second substrate with the elastic film positioned between the first substrate and the second substrate;
  (v) softening the first surface of the first substrate by the source of energy;
  (vi) positioning at least some of the softened first surface into at least one opening of the plurality of openings from the first surface of the forming die; and
  (vii) separating the forming die from the garment material to form the one or more surface protrusions integrally from the first surface of the first substrate of the garment material.

M. The method according to paragraph L, wherein the source of energy comprises induction heating, ultrasonic vibrations, micro waves, radio waves, infrared waves, a laser beam, an electron beam, or combinations thereof.

N. The method according to paragraphs L or M, wherein the configuration of the plurality of openings comprise a circle, an ellipse, an oval, a triangle, a rectangle, an extended rectangle, a polygon, a bore, a slot, or combinations thereof.

O. The method according to any of paragraphs L-N, further comprising:
advancing the elastic film to a spreader mechanism, the elastic film comprising a first edge and a second edge separated from the first edge in a cross direction by a central region;
stretching the elastic film at the spreader mechanism in the cross direction to a first elongation;
advancing the elastic film from the spreader mechanism to the forming die; and
consolidating the elastic film to a second elongation in the cross direction, wherein the second elongation is less than the first elongation, and wherein the elastic film remains stretched in the cross direction at the second elongation.

P. The method according to paragraph O, wherein the spreader mechanism comprises a ring rolling apparatus and a first disk and a second disk canted relative each other, each disk comprising an outer rim, wherein as the first and second disks rotate, the outer rims are separated from each other by a distance that increases from a minimum distance at a first location to a maximum distance at a second location.

Q. The method according to paragraph P, further comprising:
advancing the elastic film from the ring rolling apparatus to the first disk and the second disk; and
consolidating the elastic film to the second elongation by advancing the elastic film on the rotating first disk and second disk downstream of the second location.

R. The method according to any of paragraphs L-Q, wherein the garment material comprises a section of nonwoven web material, the section of nonwoven web material comprising filaments of polymeric material.

S. The method according to any of paragraphs L-R, wherein the garment material comprises a diaper, the diaper comprising a loops material section, and the one or more surface protrusions comprise an array of hooks configured to fasten to the loops material section.

T. The method according to any of paragraphs L-S, further comprising coating the one or more surface protrusions with a release agent.

U. The method according to any of paragraphs L-T, wherein the one or more surface protrusions comprise hooks, the garment material comprises a nonwoven material, the source of energy comprises an ultrasonic horn, a linear horn, a rotary horn, or combinations thereof, and the first surface of the forming die comprises an outer circumferential surface of a roll, the roll configured for rotation at a variable angular velocity.

V. A method for mechanically forming one or more surface protrusions integrally from a garment material, the one or more surface protrusions extending outwardly from a garment surface of the garment material, the method comprising:
i) placing at least one selected area of the garment surface against a first surface of a forming die, the first surface having a plurality of openings which have a configuration and orientation corresponding with the configuration and orientation of the one or more surface protrusions of the garment material;
ii) softening the garment surface by application of a source of energy, wherein the source of energy comprises at least two sonotrodes mounted in a rotary drum;
iii) positioning at least some of the softened garment surface into at least one opening of the plurality of openings from the first surface of the forming die; and
iv) separating the forming die from the garment surface to form the one or more surface protrusions.

W. The method according to paragraph V, wherein the source of energy comprises induction heating, ultrasonic vibrations, micro waves, radio waves, infrared waves, a laser beam, an electron beam, or combinations thereof.

X. The method according to paragraphs V or W, wherein the configuration of the plurality of openings comprise a circle, an ellipse, an oval, a triangle, a rectangle, an extended rectangle, a polygon, a bore, a slot, or combinations thereof.

Y. The method according to any of paragraphs V-X, wherein the garment surface comprises a section of nonwoven web material, the section of nonwoven web material comprising filaments of polymeric material.

Z. The method according to paragraph Y, further comprising combining the section of nonwoven web material with a radiofrequency receptor and exposing the section of nonwoven web material to radioactivity.

AA. The method according to any of paragraphs V-Z, further comprising coating the one or more surface protrusions with a softening agent, utilizing one or more melt additives in the garment material, or combinations thereof.

BB. The method according to any of paragraphs V-AA, wherein the one or more surface protrusions comprise hooks, the garment material comprises a nonwoven material, the source of energy comprises an ultrasonic horn, a linear horn, a rotary horn, or combinations thereof, and the first surface of the forming die comprises an outer circumferential surface of a roll, the roll configured for rotation at a variable angular velocity.

CC. The method according to any of paragraphs V-BB, wherein the forming die comprises a rotary form.

DD. The method according to any of paragraphs V-CC, wherein the forming die comprises one or more anvils disposed about and configured to rotate with the rotary drum.

EE. The method according to any of paragraphs V-DD, further comprising coating at least one opening of the plurality of openings with a release agent.

FF. The method according to any of paragraphs V-EE, further comprising treating the one or more surface protrusions with radiation for crosslinking.

GG. The method according to any of paragraphs V-FF, further comprising pre-heating the at least one selected area of the garment material.

HH. A method for mechanically forming one or more surface protrusions integrally from a garment material, the one or more surface protrusions extending outwardly from a garment surface of the garment material, the method comprising:
i) placing at least one selected area of the garment surface against a first surface of a forming die, the forming die of a linear form and having the first surface, the first surface having a plurality of openings which have a configuration and orientation corresponding with the configuration and orientation of the one or more surface protrusions of the garment material, the linear form of the forming die disposed on a conveyor assembly;

ii) softening the garment surface by application of a source of energy, the source of energy including a modular form configured for an extended contact with the linear form of the forming die when conveyed by the conveyor assembly compared to a non-modular form;

iii) positioning at least some of the softened garment surface into at least one opening of the plurality of openings from the first surface of the forming die; and iv) separating the forming die from the garment surface to form the one or more surface protrusions.

II. The method according to paragraph HH, wherein the source of energy comprises induction heating, ultrasonic vibrations, micro waves, radio waves, infrared waves, a laser beam, an electron beam, or combinations thereof.

JJ. The method according to paragraphs HH or II, wherein the configuration of the plurality of openings comprise a circle, an ellipse, an oval, a triangle, a rectangle, an extended rectangle, a polygon, a bore, a slot, or combinations thereof.

KK. The method according to any of paragraphs HH-JJ, wherein the garment surface comprises a section of nonwoven web material, the section of nonwoven web material comprising filaments of polymeric material.

LL. The method according to any of paragraphs HH-KK, further comprising coating at least one opening of the plurality of openings with a release agent.

MM. The method according to any of paragraphs HH-LL, further comprising treating the one or more surface protrusions with radiation.

NN. The method according to any of paragraphs HH-MM, wherein the one or more surface protrusions comprises at least one hook, the garment material comprises a nonwoven material, and the source of energy comprises an ultrasonic horn, a linear horn, or combinations thereof.

OO. The method according to any of paragraphs HH-NN, wherein separating the forming die from the garment surface occurs at an infeed speed different from an outfeed speed at which the at least one selected area of the garment surface is placed against the first surface of the forming die such that the difference in the infeed speed and the outfeed speed causing a variable speed when the at least some of the softened garment surface are positioned into the plurality of openings.

PP. The method according to paragraph OO, wherein the variable speed is slower than the infeed speed.

QQ. The method according to any of paragraphs HH-PP, further comprising pre-heating the at least one selected area of the garment material.

It is noted that the terms "substantially" and "about" and "approximately" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method for assembling elastic laminates and mechanically forming one or more surface protrusions integrally from a garment material, the one or more surface protrusions extending outwardly from a first surface of the garment material, the method comprising:

(i) wrapping the first surface of a first substrate of the garment material onto an outer circumferential surface of a forming die, the forming die having a first surface, the first surface having a plurality of openings which have a configuration and orientation corresponding with the configuration and orientation of the one or more surface protrusions of the garment material;

(ii) advancing an elastic film to a spreader mechanism, the elastic film comprising a first edge and a second edge separated from the first edge in a cross direction by a central region; stretching the elastic film at the spreader mechanism in the cross direction to a first elongation; advancing the elastic film from the spreader mechanism to the forming die and positioning the elastic film in contact with a second surface of the first substrate on the forming die; and consolidating the elastic film to a second elongation in the cross direction, wherein the second elongation is less than the first elongation, and wherein the elastic film remains stretched in the cross direction at the second elongation;

(iii) advancing a second substrate to position a first surface of the second substrate in contact with the elastic film and the second surface of the first substrate on the forming die;

(iv) ultrasonically bonding by a source of energy the first substrate together with the second substrate with the elastic film positioned between the first substrate and the second substrate;

(v) softening the first surface of the first substrate by the source of energy;

(vi) positioning at least some of the softened first surface into at least one opening of the plurality of openings from the first surface of the forming die; and separating the forming die from the garment material to form the one or more surface protrusions integrally from the first surface of the first substrate of the garment material.

2. The method of claim 1, wherein the source of energy comprises induction heating, ultrasonic vibrations, micro waves, radio waves, infrared waves, a laser beam, an electron beam, or combinations thereof.

3. The method of claim 1, wherein the configuration of the plurality of openings comprise a circle, an ellipse, an oval, a triangle, a rectangle, an extended rectangle, a polygon, a bore, a slot, or combinations thereof.

4. The method of claim 1, wherein the spreader mechanism comprises a ring rolling apparatus and a first disk and a second disk canted relative each other, each disk comprising an outer rim, wherein as the first and second disks rotate, the outer rims are separated from each other by a distance that increases from a minimum distance at a first location to a maximum distance at a second location.

5. The method of claim 1, wherein the garment material comprises a section of nonwoven web material, the section of nonwoven web material comprising filaments of polymeric material.

6. The method of claim 1, further comprising coating the one or more surface protrusions with a release agent.

7. The method of claim 1, wherein the one or more surface protrusions comprise hooks, the garment material comprises a nonwoven material, the source of energy comprises an ultrasonic horn, a linear horn, a rotary horn, or combinations thereof, and the first surface of the forming die comprises an outer circumferential surface of a roll, the roll configured for rotation at a variable angular velocity.

8. The method of claim 1, wherein the source of energy comprises one or more sonotrodes, and the forming die comprises a rotary form.

9. The method of claim 1, wherein the source of energy comprises one or more sonotrodes mounted in a rotary drum, and the forming die comprises one or more anvils disposed about the rotary drum.

10. The method of claim 1, wherein the source of energy comprises at least two sonotrodes that are static relative to the forming die.

11. The method of claim 1, further comprising treating the one or more surface protrusions with radiation for crosslinking.

12. The method of claim 4, further comprising:
advancing the elastic film from the ring rolling apparatus to the first disk and the second disk; and
consolidating the elastic film to the second elongation by advancing the elastic film on the rotating first disk and second disk downstream of the second location.

13. The method of claim 5, wherein the garment material comprises a diaper, the diaper comprising a loops material section, and the one or more surface protrusions comprise an array of hooks configured to fasten to the loops material section.

* * * * *